(12) United States Patent
Levitt et al.

(10) Patent No.: US 11,167,225 B2
(45) Date of Patent: Nov. 9, 2021

(54) PLANT TRICHOME FILTRATION AND CONCENTRATION

(71) Applicant: Spiral Water Technologies, Inc., Middlesex, NJ (US)

(72) Inventors: David Levitt, San Anselmo, CA (US); Jamie Yosha, Fairfax, CA (US)

(73) Assignee: Spiral Water Technologies, Inc., Middlesex, NJ (US)

( * ) Notice: Subject to any disclaimer, the term of this patent is extended or adjusted under 35 U.S.C. 154(b) by 114 days.

(21) Appl. No.: 16/745,869

(22) Filed: Jan. 17, 2020

(65) Prior Publication Data
US 2020/0230530 A1    Jul. 23, 2020

Related U.S. Application Data

(60) Provisional application No. 62/794,264, filed on Jan. 18, 2019.

(51) Int. Cl.
| *B01D 29/23* | (2006.01) |
| *B01D 29/64* | (2006.01) |
| *B01D 11/02* | (2006.01) |
| *C07C 37/00* | (2006.01) |
| *C07D 311/78* | (2006.01) |

(52) U.S. Cl.
CPC .......... *B01D 29/23* (2013.01); *B01D 11/0203* (2013.01); *B01D 11/0288* (2013.01); *B01D 29/6415* (2013.01); *B01D 29/6476* (2013.01); *C07C 37/004* (2013.01); *C07D 311/78* (2013.01)

(58) Field of Classification Search
CPC ............... B01D 29/23; B01D 29/6476; B01D 29/6415; B01D 11/0203; B01D 11/0288; B01D 29/25; B01D 29/902; B01D 29/904; B01D 2201/583; C07C 37/004; C07D 311/78
See application file for complete search history.

(56) References Cited

U.S. PATENT DOCUMENTS

| 9,409,106 B2 * | 8/2016 | Levitt .................. B01D 29/606 |
| 2019/0054393 A1 * | 2/2019 | Camilleri ........... B01D 11/0257 |

* cited by examiner

*Primary Examiner* — John M Mauro
(74) *Attorney, Agent, or Firm* — Knobbe, Martens, Olson & Bear LLP

(57) ABSTRACT

Trichomes, lupulins and other plant parts can be efficiently separated from plant biomass by continuous filtration. In some embodiments plant biomass is collected and combined with water to form a plant biomass mixture. The plant biomass mixture is passed through a filtration device in which the plant biomass mixture is continuously flowed through a filter material. The device includes a cleaning apparatus that cleans the filter material during the process. In some embodiments greater than 90% of the plant parts are collected from the starting plant biomass. The plant parts can be subsequently processed to obtain desired compounds. For example, trichomes can be separated from other plant biomass and subsequently processed to extract one or more cannabinoids or terpenes, such as THC and/or CBD.

20 Claims, 26 Drawing Sheets

PLANT TRICHOME FILTRATION AND CONCENTRATION

REFERENCE TO RELATED APPLICATIONS

The present application claims priority to U.S. Provisional Application No. 62/794,264, filed Jan. 18, 2019, which is hereby incorporated by reference in its entirety.

BACKGROUND

Field of the Invention

The present application relates to the filtration of particles from fluid streams, and more specifically to methods and filter systems for removing plant parts, such as trichomes, from plant biomass.

Description of the Related Art

Filter systems contain cleaning devices, such as cleaning brushes, suction scanning devices, and back flush mechanisms. These devices are driven by various means including by hand, motor, turbine or vortex. However, existing fluid filtration devices have difficulty handling large concentrations of solids in the fluid stream. Generally cleaning mechanisms which can operate continuously while the system is filtering out-perform those which require the filtration system to be stopped for cleaning. Nevertheless, existing continuous cleaning mechanisms often suffer from premature fouling when the particle accumulation rate exceeds their limited cleaning rates.

SUMMARY OF THE INVENTION

In some aspects methods and devices are provided for separating small plant parts, such as trichomes and lupulins, from other plant material. In some embodiments plant material is passed through a filtration device as described herein, comprising a filter screen and a housing, and the desired plant parts are collected at one end of the housing of the filtration device. In some embodiments fluid is continuously passed through the filter screen during the filtration process. In some embodiments the desired plant parts are trichomes. In some embodiments the desired plant parts are lupulins. In some embodiments the screen has a nominal gap width of 15 microns. In some embodiments a purge valve is opened intermittently to collect trichomes or other plant parts that have been collected. In some embodiments a rotating cleaning assembly cleans the filter screen during the filtration process. The use of the rotating cleaning assembly can facilitate continuous fluid flow through the filter screen during the filtration process. In some embodiments more than 99% of the desired plant parts, such as mature trichomes, are removed from a water mixture comprising plant biomass. In some embodiments the desired plant parts are collected after filtration and are dewatered using a filter bag, dewatering sack, belt filter press or other device. In some embodiments the desired plant parts that have been collected are dried, such as by air drying or freeze drying. The isolated plant parts may be subject to subsequent processing. For example, collected trichomes may subsequently be subjected to an extraction process.

In some embodiments methods of collecting trichomes from plant biomass are provided. Plant biomass may be prepared from cannabis plants, for example by trimming selected cannabis plants and milling or chopping the plant material. The obtained biomass may be combined with water and agitated. In some embodiments the water is chilled, such as below room temperature or below 25° C. In some embodiments a plant biomass mixture comprising greater than 500 ppm trichomes is provided. A filtration device as described herein may be used to filter the trichomes from the plant biomass mixture. In some embodiments prior to filtration in the filtration device, the plant biomass mixture is passed through one or more filters each comprising pores of at least 100 microns.

In some embodiments the filtration device comprises a housing having an unfiltered inlet and a filtered outlet. The device may also comprise an annular filter located within the housing and a rotating cleaning assembly located within the annular filter. The cleaning assembly may also comprise a distributor for providing the biomass mixture to the filter. In some embodiments the filter material may have a gap width of about 10 to 25 microns. In some embodiments the filter material may be an electroformed screen.

In some embodiments the trichomes are filtered from the plant biomass mixture by directing the mixture through the distributor to an inside surface of the filter. The plant biomass mixture is passed through the filter and filtered material comprising trichomes is collected at the filtered outlet. In some embodiments the cleaning assembly is rotated inside the filter such that the inside surface of the filter is cleaned. In some embodiments greater than 50%, 60%, 70%, 80%, 90%, 95% or 99% of the trichomes are removed from the plant biomass mixture and collected by filtration. In some embodiments greater than 50% of the collected filtered material is trichomes by weight.

In some embodiments the plant biomass mixture is continuously fed to the inside surface of the filter during filtering. In some embodiments the cleaning assembly is continuously utilized during filtering, such as by continuously rotating the cleaning assembly during filtering. In some embodiments the cleaning assembly comprises a wiper, such as a brush.

Following filtration the filtered trichomes may be dewatered and/or dried. One or more compounds such as terpenes and/or cannabinoids may be extracted from the filtered trichomes. In some embodiments CBD and/or THC is extracted from the filtered trichomes. Extraction may be done, for example, by supercritical CO2 extraction, ethanol extraction or butane extraction.

In some embodiments on or more plant parts, such as trichomes or lupulins, are purified from plant biomass comprising the plant parts by mixing the plant biomass with water or other liquid to form a plant biomass mixture. The plant biomass mixture is continuously fed into a filtration device comprising a housing comprising a filter and a cleaning assembly. The plant biomass mixture is fed through the filter and the one or more plant parts are collected. In some embodiments more than 90% of the plant parts in the plant biomass are collected. In some embodiments the filter has a gap width of about 10 to 25 microns. The cleaning assembly may operate to continuously clean the filter during the filtering process.

BRIEF DESCRIPTION OF THE DRAWINGS

In the attached figures various embodiments are illustrated by way of example. Like reference numerals refer to similar elements.

DETAILED DESCRIPTION

Figure 1:
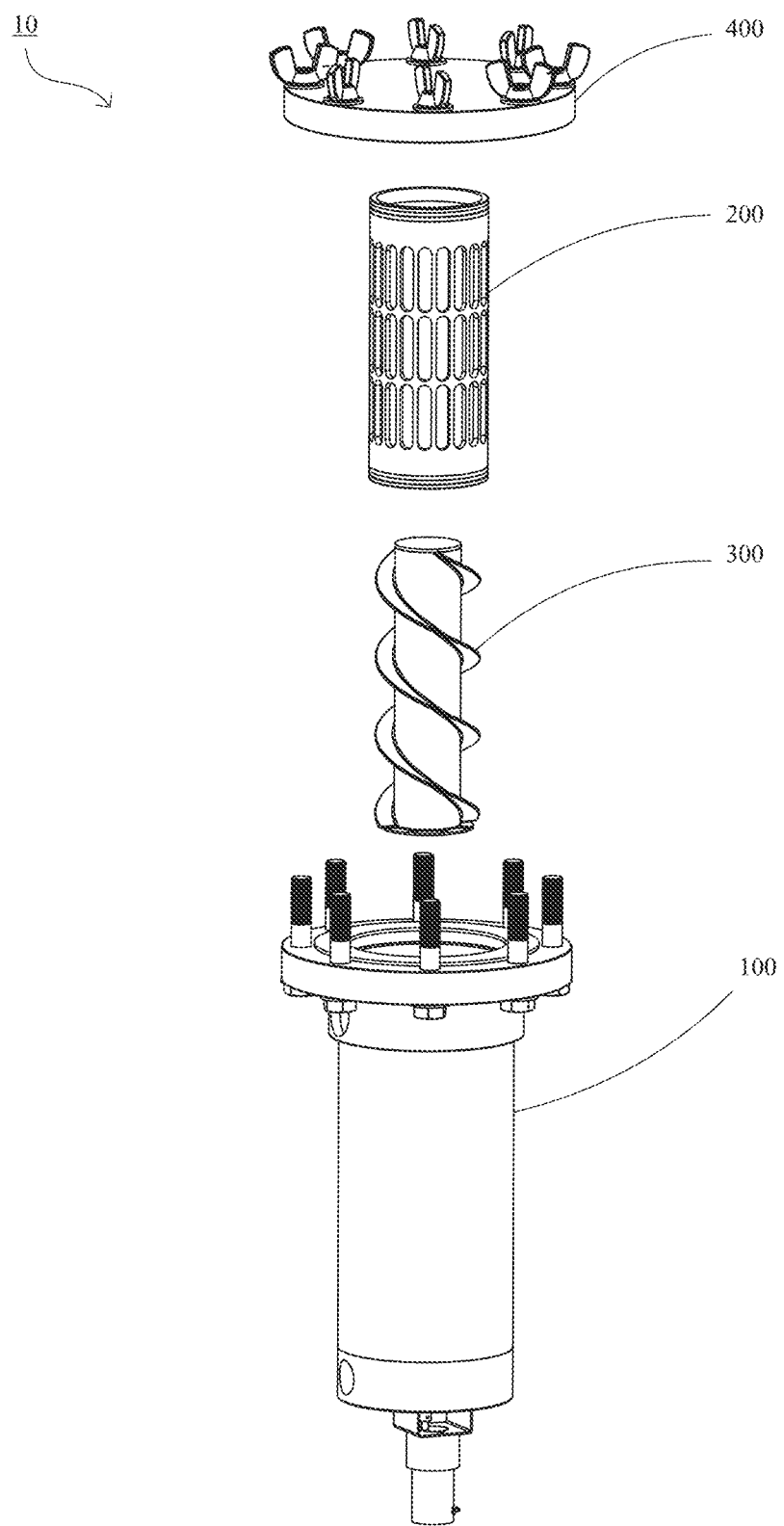
FIG. 1 is an exploded view illustrating each of the major components of one embodiment of a filter system.

The methods, systems and components described herein relate to filter systems for separating solids from fluids. The fluids may comprise air or other gas; or water, oil, fuel or other liquid. In some applications the filtered fluid is the end product. Such applications may include, but are not limited to, drinking water, wastewater, recycled water, irrigation, swimming pools, food and beverage processing, produced water from oil and gas production, cooling towers, power plants, and marine ballast or bilge water. By way of example, drinking water is often produced by a series of filters removing ever finer particles and contaminants. A first or second level of filtration may comprise an automatic strainer to remove particles down to 10 microns in diameter. The filtered water would then be conveyed to a finer filter like an ultrafilter, microfilter or reverse osmosis filter. Some embodiments of the filter systems described herein are well suited to this application.

In other applications, such as biofuel production and other biomass technologies, a particulate is separated from a fluid stream and the filtered solid is the desired product. By way of example, algae may be harvested from the water in which it's growing for the purposes of making biodiesel. The algae is first filtered from the water and concentrated to form a slurry. The oil is extracted from the algae by solvent extraction or other means, and then converted into biodiesel through a chemical process called transesterification. Some embodiments of the filter systems described herein are well suited to remove algae from its liquid growth media for these purposes.

In some embodiments, plant biomass is processed and desired plant parts are separated and collected. For example, trichomes or lupulins may be separated from plant biomass. The desired plant parts, such as trichomes or lupulins, may be subject to further processing, such as extraction of desired components. In some embodiments plant biomass is prepared from one or more plants, such as one or more cannabis or hops plants, and subject to filtration as described herein. In some embodiments mature trichomes are separated from other plant biomass, including from immature or undeveloped trichomes, and collected. In some embodiments lupulins are separated from other plant biomass and collected. Collected plant material, such as lupulins and trichomes, can be further processed such as by dewatering, drying and extraction of desired compounds, such as terpenes or cannabinoids.

In some embodiments plant biomass is prepared from one or more cannabis plants and mature trichomes are separated and collected by filtration. The collected mature trichomes may be dewatered. One or more compounds, such as one or more cannabinoids and/or terpenes, may be extracted from the collected trichomes. In some embodiments cannabidiol (CBD) is extracted from the separated and collected trichomes.

In some embodiments plant biomass is prepared from one or more hops plants and lupulins are separated and collected by filtration. The collected lupulins may be dewatered and one or more compounds of interest may be extracted from the collected lupulins. In some embodiments lupulin or lupinol is extracted from the separated and collected lupulins.

Housing and Lid Assembly

In some embodiments, a filter system comprises a hollow housing and a hollow filter assembly. The filter system may also comprise a cleaning assembly and a lid assembly. One embodiment of such a filter system is illustrated in FIG. 1. The filter system 10 as illustrated in FIG. 1 comprises a hollow housing 100, a hollow filter assembly 200, a cleaning assembly 300, and a lid assembly 400.

The hollow housing may take any of a variety of shapes. In the illustrated embodiment the hollow housing 100 is generally cylindrical in shape and may comprise one or more parts coupled together, such as by fasteners, a v-band clamp or other suitable connectors. Additionally the illustrated filter system 10 has a lid assembly 400 at one end of the housing 100 which can also couple to the housing 100, for example by one or more fasteners, a v-band clamp, or other suitable connectors. The housing 100 and lid assembly 400 may be fabricated from one or more of a variety of materials, examples of which are plastic, fiber glass, stainless steel, and epoxy coated steel.

The filter assembly is shaped to fit within the hollow housing and in some embodiments is annular in shape. As illustrated, the filter assembly 200 takes the shape of a hollow cylinder and is located inside and concentric with the housing 100. The filter assembly 200 comprises a filter material, such as a filter membrane, and in some embodiments may comprise a filter frame or other support structure. In some embodiments the filter assembly is generally open at both ends and contacts the housing, for example through a seal at one or both ends. Examples of seals are o-rings, x-rings, u-cups and gaskets. In the illustrated embodiment, the filter assembly 200 seals to the housing 100 at one end and the lid assembly 400 at the other end. The lid as well as the other end of the housing can be flat, semi-elliptical, hemispherical, or other suitable shape.

The housing and lid combination have one or more each of an inlet, a filtered outlet and a drain outlet. In some embodiments one or more inlets are generally located at one end of the filter system, while one or more filtered outlets and drain outlets are generally located at opposite ends of the filter system from the one or more inlets. In other embodiments, other arrangements may be used. The one or more inlets and outlets may be positioned on any combination of the side wall of the housing, the end of the housing, and the lid. Inlets provide a path for fluid to flow from a source to the interior of the filter assembly where it contacts the working surface of the filter material. The filtered outlet provides a path for fluid that has passed through the filter material to exit the housing. Drain outlets provide a path for fluid and/or solids that do not pass through the filter material to be removed from the housing.

Figure 2:
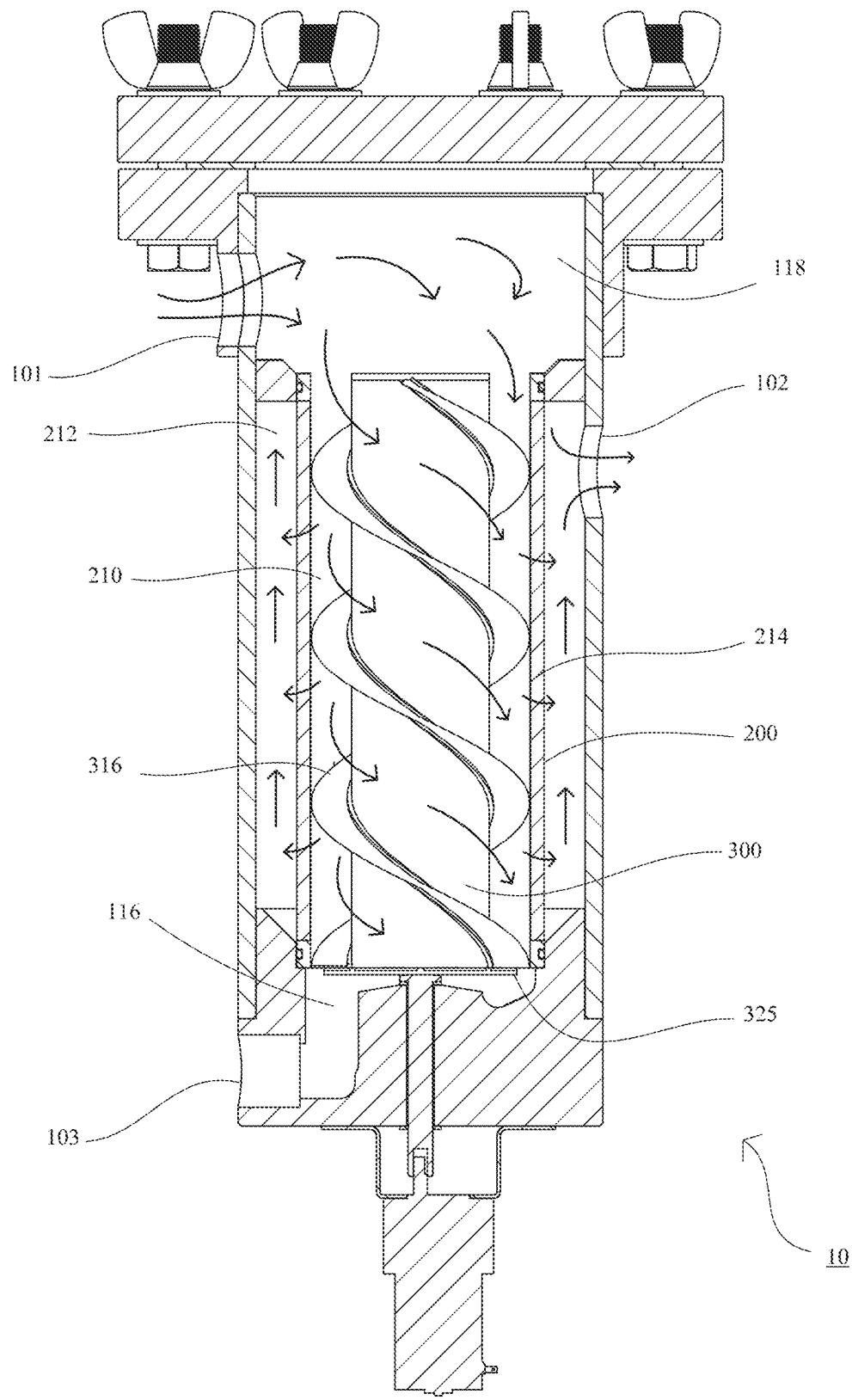
FIG. 2 is an illustration of one embodiment of the filter system where the filter is sealed to the housing at either end, and the cleaning assembly comprises wipers. The housing, filter and lid are shown in cutaway form while the cleaning assembly is not.
Figure 3:
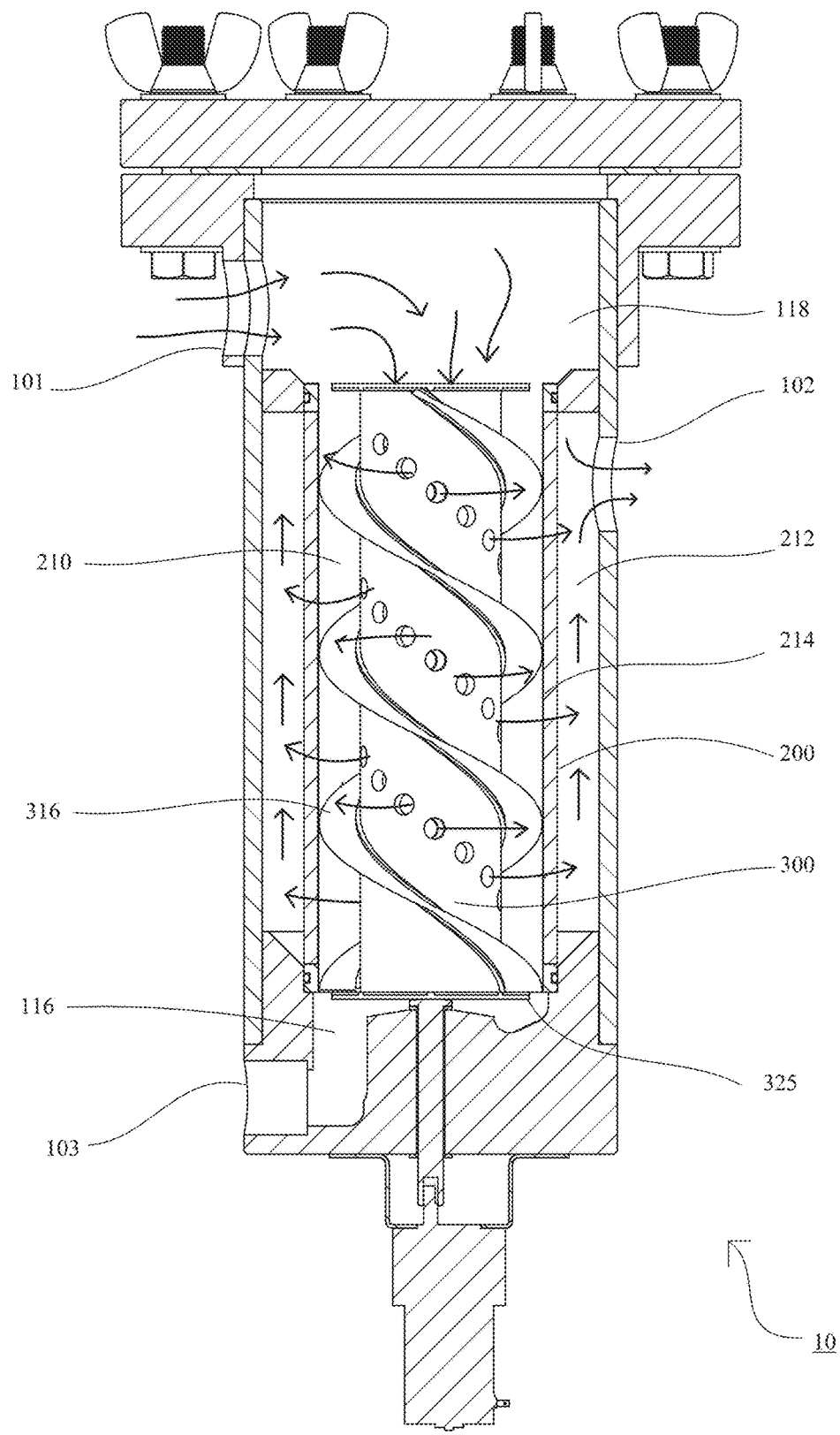
FIG. 3 is an illustration of another embodiment of the filter system where the filter assembly is sealed to the housing at either end, and the cleaning assembly comprises wipers and a distributor. The housing, filter and lid are shown in cutaway form while the cleaning assembly is not.
Figure 4:
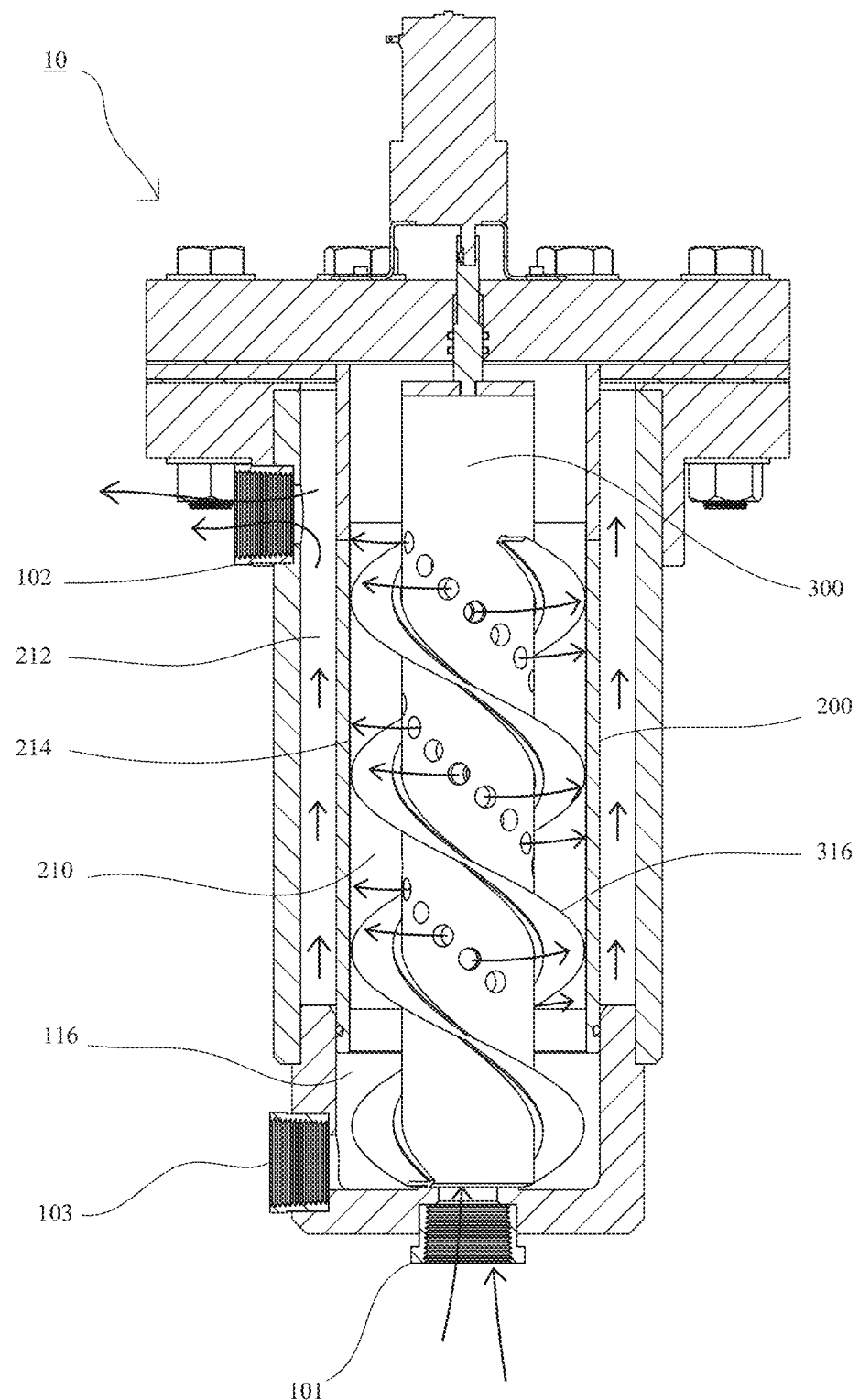
FIG. 4 is an illustration of an embodiment of the filter system where the filter assembly is sealed to the housing at one end and the lid at the other end, and the cleaning assembly comprises wipers and a distributor. The housing, filter and lid are shown in cutaway form while the cleaning assembly is not.

When the filter assembly is sealed to the housing, as illustrated in FIGS. 2 and 3, or the housing and lid as illustrated in FIG. 4, an unfiltered influent region 210 and a filtered effluent region 212 are created which communicate only through the filter material 214. The inlet 101, inlet region 118 and drain outlet 103 communicate with the influent region 210 at the inside of the filter 214, while the filtered outlet 102 communicates with the filtered effluent region 212 at the outside of the filter 214. The drain outlet 103 may be in communication with a collection region 116 where unfiltered fluid and filtered solids collect. Solids that collect on the working surface of the filter material 214 during operation of the filter system 10 may be moved by the action of wipers 316 to the collection region. A divider 325 may be located between the collection region 116 and the unfiltered region 210. In some embodiments, for example when the filtered fluid is a liquid, the filtered outlet 102 is located and the housing oriented to facilitate the expulsion of air from the system. This can be accomplished, for example, by positioning the filtered outlet 102 at or above the highest point of the filter material 214. In this way there is little to no need for an air purge valve. However, such an orientation of the filtered outlet 102 and housing are not required and in some embodiments the housing 100 comprises an air purge valve.

FIGS. 2 and 3 illustrate embodiments where the inlet 101 is located at the same end of the housing as the filtered outlet 102, albeit on opposite side walls. FIG. 4 illustrates another embodiment where the inlet 101 is located at the same end of the housing as the drain outlet 103.

Filter Assembly

Figure 5:
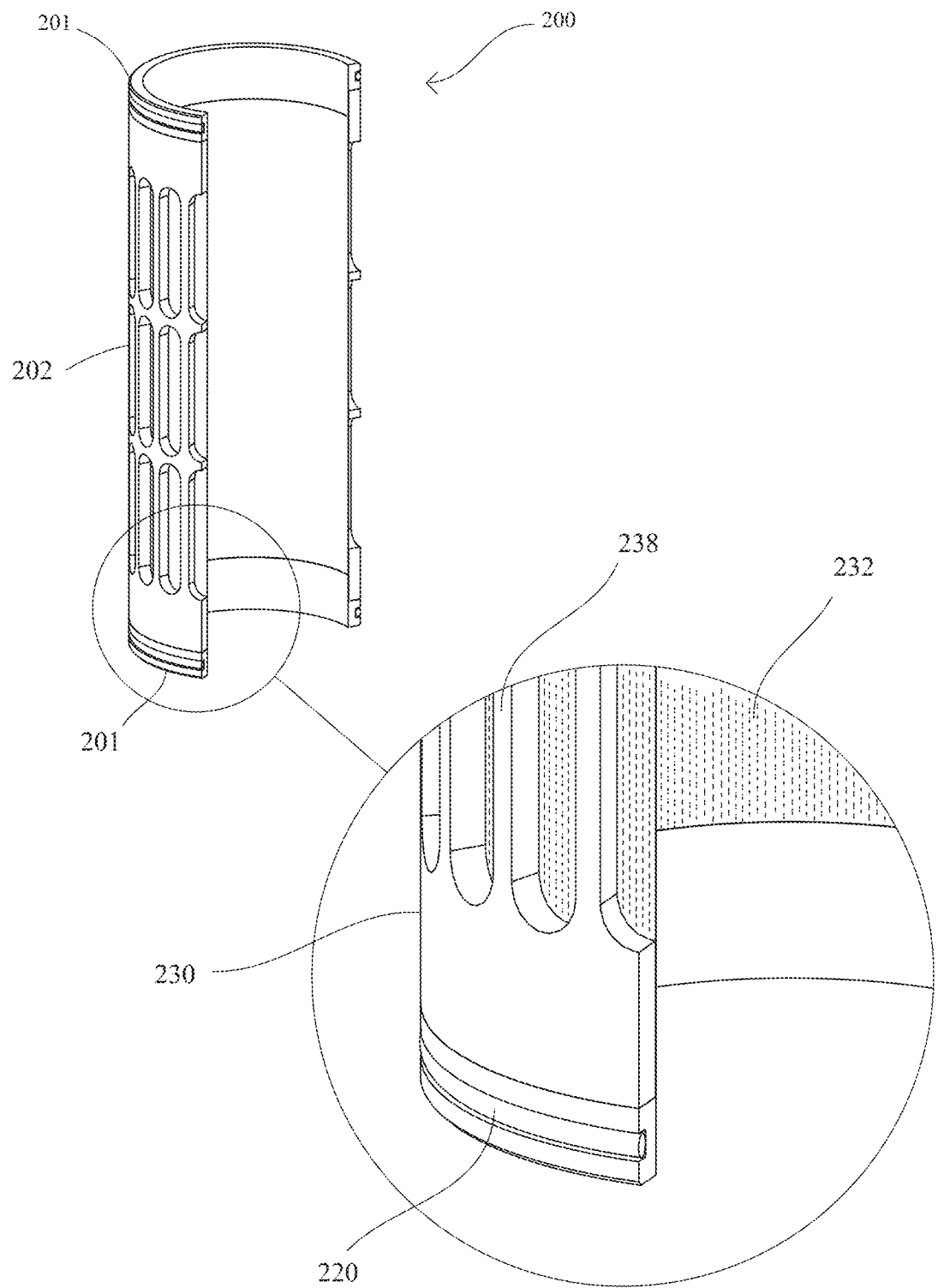
FIG. 5 illustrates an embodiment of the filter assembly comprising a filter support structure and a filter material.

In some embodiments a hollow cylindrical filter assembly 200 comprises a filter material 232 and a support structure 230, as illustrated in FIG. 5. In some embodiments, however, the filter material 232 will not require a support structure 230 and thus a support structure will not be used. In some embodiments the filter material is a surface filter. In the embodiments illustrated in FIGS. 2, 3 and 4, fluid passes from the influent region 210 at the inside of the filter to the effluent region 212 at the outside of the filter. In this way filtered particles collect on the inner, working surface of the filter 214. Suitable filter materials include but are not limited to electroformed screens, stacked disc filters, fabrics and membranes, woven metals, etched metal screens, and wedge wire filters. The filter material may be arranged to form an annular structure, as in the embodiment illustrated in FIG. 5.

In some embodiments a support structure is used. For example, with thin filter materials, such as screens, fabrics and other membranes, a support structure may be used to maintain the desired shape, typically an annular or cylindrical shape. The support structure may also contain seals at each end of the filter or make contact with seals at each end of the housing. In some embodiments a PVC plastic support structure is used to support a hollow cylindrical filter material. In other embodiments, a support structure comprises openings, where the openings are covered with the filter material.

A support structure may consist of one or more parts. As illustrated in FIG. 5, the support structure 230 may be assembled from three pieces which include two solid tubular end caps 201 and a supportive mid section 202 with a mesh of ribs 238. The end caps 201 may each comprise a seal. For example, each end cap 201 may have an o-ring groove to contain an o-ring seal 220. In embodiments where the support 230 is made of PVC, PVC solvent cement may be used to join the three structural pieces and simultaneously capture the open ends of the filter material cylinder. In other embodiments of the filter assembly the filter material is placed in an injection mold and the frame is molded directly onto the filter material in one or more stages. A plastic frame can be made from any number of suitable plastics including, for example, PVC, polypropylene and polycarbonate. In other embodiments of the invention the one or more support structure parts are made from stainless steel or other suitable materials and welded or bonded to the filter material. In further embodiments the supportive midsection is made from an overwrap of a screen material which can be, for example, plastic or metal and can be welded or bonded to the filter material. In other embodiments the filter material may be supported by a wedge wire wrapped in a spiral shape around the outside of the filter material.

The difference in pressure across the filter material, also referred to herein as transmembrane pressure (even though the filter material is not always a membrane), causes flow through the filter material. The transmembrane pressure is typically maintained at a constant value throughout the filtering process, but may be varied in certain circumstances, such as for cleaning. In some embodiments the transmembrane pressure may be about 10 psi or less, for example about 0.1 to 10 psi. In other embodiments the transmembrane pressure may be about 0.1 to 3 psi, 0.1 to 2 psi, or 0.1 to 1 psi. A sudden jump in the pressure can occur if the filter suddenly plugs. For this reason the filter is generally designed to sustain differential pressures in the range of at least 20 to 30 psi, but in some embodiments may sustain pressures as high as 150 psi or more.

As mentioned above, suitable filter materials include but are not limited to electroformed screens, stacked disc filters, fabrics and membranes, such as plastic fabrics and membranes, woven metals, etched metal screens, and wedge wire filters. In some embodiments, the filter material comprises pores or gaps with a maximum width of about 0.1 micron to about 1500 microns. In other embodiments, the pores or gaps may have a maximum width of about 1 to about 500 microns or about 1 to about 50 microns. In some embodiments the pores or gaps are about 1 to about 20 microns. In some embodiments, for example for the processing of plant material, the pores or gaps are about 10 to 20 microns. In some embodiments the pores or gaps are about 12 to 18 microns. In some embodiments the pores or gaps are about 15 microns. In some embodiments plant biomass is processed to collect trichomes and/or lupulins and the filter comprises pores or gaps of about 12 to 18 microns, or about 15 microns.

The variation in pore width across a filter can be an important feature of the filter material. In some embodiments the absolute variation in pore width is minimized. It is also common to measure the variation as a percentage of pore width. In some embodiments the variation in pore width may range from about ±1% to about ±30%. In other embodiments such as with precision electroformed screens the precision may be measured in microns ranging from about ±0.1 micron to about ±5 microns. In some embodiments the filter material comprises expanding pores, which are narrower at the working surface than at the opposite surface. However, a variety of pore shapes may be used and a filter material having pores with an appropriate width, shape and other attributes can be selected by the skilled artisan for a particular application.

In some embodiments the filter material is a precision electroformed screen. The electroformed screen can be made from a number of materials for example nickel, gold, platinum and copper. A filter material of this type may comprise a substantially smooth working surface and regularly shaped expanding pores. That is, the pores are narrower at the working surface than at the opposite surface. In some embodiments the pores may be conical. Screens of this type may be used that have pores ranging in size from about 1500 microns down to about 0.1 micron at the narrowest point, but variations of the technology can utilize larger or smaller pores.

In some embodiments a screen is used for filtration in the range of 5 to 50 microns and has pores with a corresponding width at the narrowest point. In some embodiments, a screen is used for filtration in the range of 10 to 20 microns and has pores with a corresponding width at the narrowest point. In some embodiments, a screen is used for filtration in the range of 15 microns and the screen has pores with a corresponding width at the narrowest point.

In some embodiments a filter material is used that comprises a precision electroformed nickel screen. One such screen is called Veconic Plus Smooth, fabricated by and available from Stork Veco BV of The Netherlands. Veconic Plus Smooth is especially well suited to filtration in the range of about 5 to 50 microns.

Figure 6:
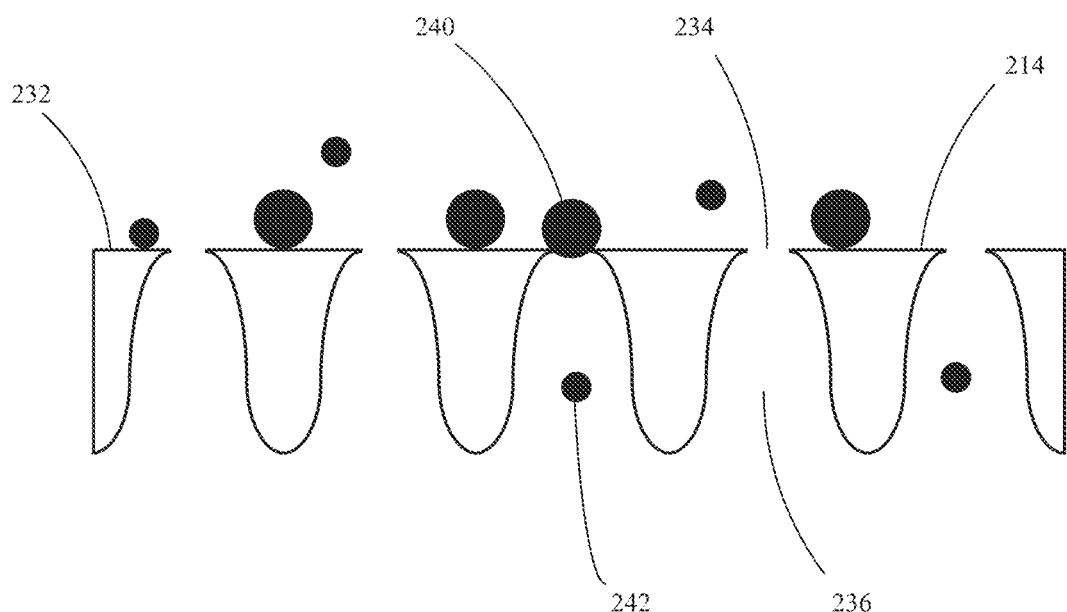
FIG. 6 is a schematic illustration of a cross-section of a filter material having a smooth working surface and expanding pores.

A filter material may comprise pores where the internal surfaces of a pore may be straight, concave or convex. In some embodiments, as illustrated in FIG. 6, the filter material 232 comprises pores where the profile of the pore is substantially narrowest at the working surface 214 of the filter. In some embodiments where the filter is a cylindrical or annular filter, the working surface may be the internal surface. The pore may remain the same width or become wider across the filter from the internal or interior working surface to the external or exterior surface. In some embodiments the pores comprise an expanding region 236 and open progressively wider from the working surface towards the opposite surface. In this way, particles 242 small enough to enter a pore opening 234 have little or no chance of getting stuck inside a pore 236. Surface filters of this type trap particles 240 that are too large to pass through the filter material on their working surface 214, often at the mouth of a pore 234, where they can be acted upon by a cleaning mechanism.

Figure 7:
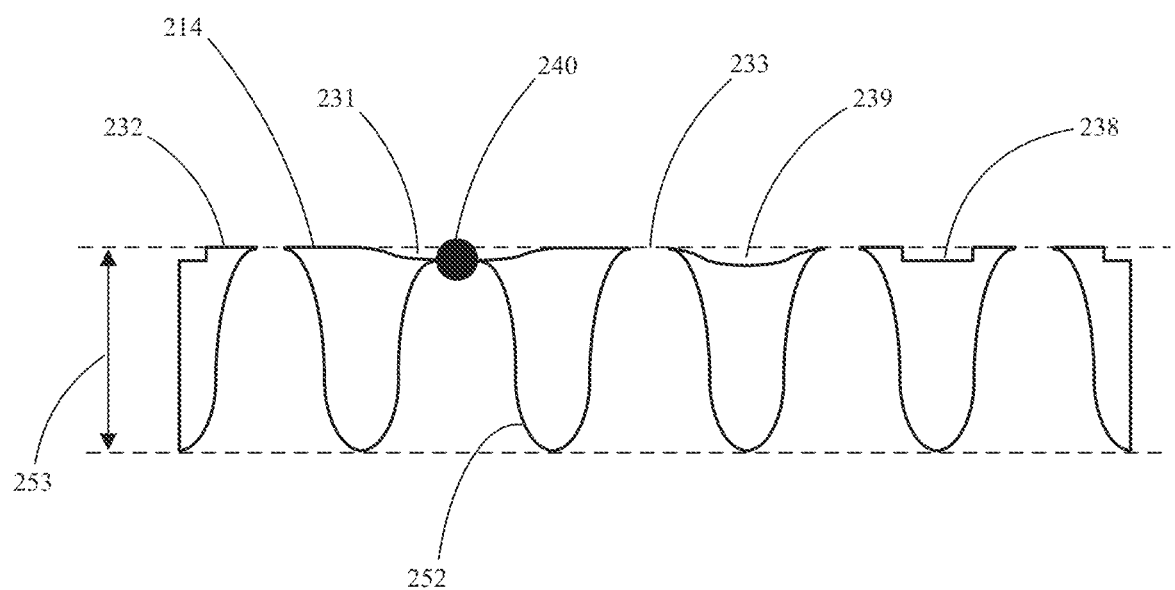
FIG. 7 is a schematic illustration of a cross-section of a filter material having expanding pores and a smooth working surface wherein the boundary of the pore opening at the minimum width of the pore opening (the narrowest part of the pore) substantially defines the highest local point on the working surface.

In some embodiments the working surface of the filter is smooth. Though the smooth working surface of the filter may be substantially flat, it may also have small, uneven features, for example as illustrated in FIG. 7. These uneven features may be sudden steps 238 or gradual valleys 239. However, the filter is preferably structured such that during filtration particles that are not able to pass through the pores are retained at the highest local point on the working surface.

In some embodiments the narrowest part of the pore opening 233 substantially defines the highest point on the working surface 214 in the vicinity of the pore. In other embodiments, the narrowest part of the pore opening 231 may be slightly below the highest local point on the smooth working surface 214, for example the narrowest part of the pore opening may be at a depth less than half the width of the pore opening. Thus, for a pore with a narrowest opening of 20 microns, the 20 micron opening would be less than 10 microns below the highest point on the smooth working surface in the vicinity of the pore. This makes it possible for a cleaning mechanism to make substantial contact with pore blocking particles 240 and wipe them away from the pore openings. The area of filter material between the pores is referred to as the bars 252.

Figure 8:
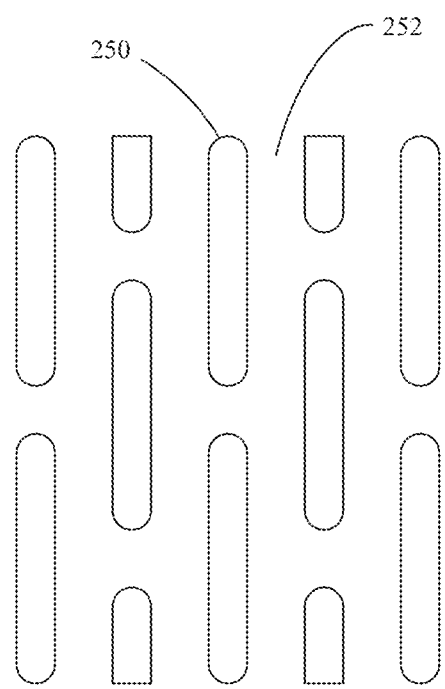
FIG. 8 illustrates a portion of the surface of a filter material comprising an alternating pattern of slotted pores.
Figure 9:
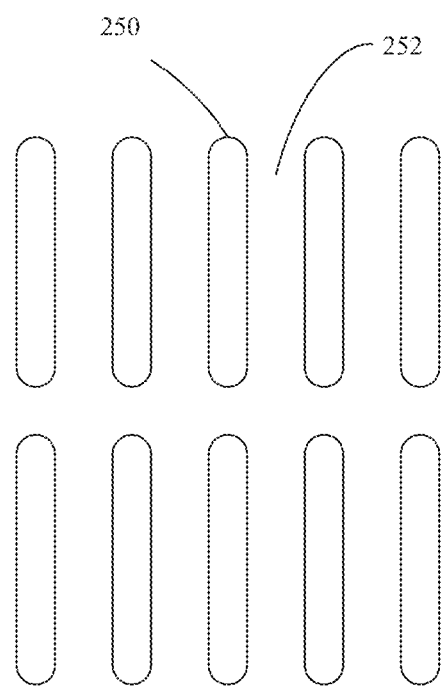
FIG. 9 illustrates a portion of the surface of a filter material comprising a non-alternating pattern of slotted pores.

The pores can have many planform shapes, examples of which are circular, square or slotted. Slotted pores 250 which are longer than they are wide, as illustrated in FIGS. 8 and 9, are used in some embodiments and tend to offer less fluid resistance than a number of smaller circular or square pores having the same combined open area. The drawback of slotted pores 250 is that they can pass long skinny particles that are essentially larger than the slot width, but these particles are much less common. Nevertheless, in some embodiments circular, square or irregularly shaped pores are used.

In some embodiments, filters may have a thickness of about 10 to 10,000 microns. This is illustrated as the bar thickness 253 in an exemplary embodiment in FIG. 7. Electroformed nickel screens, as used in some embodiments, generally have a thickness of 150 to 300 microns, though they may be thicker or thinner. A sheet of filter material has many pores, and in some embodiments substantially all of the pores have approximately the same length and width. The pores may be any shape. In some embodiments they are circular. In other embodiments the pores are longer than they are wide. In some embodiments the length of each pore is generally about 400 to 500 microns, for example about 430 microns, but may be larger or smaller. The width of the pores may be selected for the particular filtration application. In some embodiments, widths in the range of about 0.1 to about 1500, 1 to 500 or 1 to 50 microns are used. In some applications, like the harvesting of microalgae or yeast cells without flocculation, widths from about 0.1 to about 1 micron may be used.

In some embodiments the pores may be generally arranged in an alternating checkerboard pattern as with the pores 252 in FIG. 8, but may also be arranged in a non-alternating pattern, as in FIG. 9. The bars 253 are also shown in FIGS. 8 and 9. Screens with non-alternating patterns are generally more brittle than those with alternating patterns, which tend to be more flexible.

In some embodiments the cumulative open area of all the pores for a filter material is maximized in order to maximize the filtrate rate. For smaller pores the number of pores per unit length can be maximized in any given direction. With many screens, such as electroformed nickel screens that have expanding pores, the maximum open area of pores tends to be inversely proportional to the sheet thickness, i.e. thicker sheets have fewer pores. The number of pores per unit length in a given direction is influenced by many variables, one of which is the lithographic process by which the screens are made.

In some embodiments a screen may have a thickness of about 200 microns with pores which are about 20 microns wide by about 430 microns long and arranged in a mesh of about 160 pores per inch (6299 $m^{-1}$) in the direction perpendicular to the slots and about 40 pores per inch (1575 $m^{-1}$) parallel to the slots. This equates to an open area of about 9%.

In some embodiments the filter material takes the form of a hollow structure such as a hollow cylindrical or annular structure. Seamless hollow cylinders can be used and can be fabricated, for example, in an electroforming process. In other embodiments, cylinders can be made from sheets of filter material which are then seam welded into a cylinder. Methods of joining seam edges are known in the art and may include, for example, resistance welding or soldering. In this way cylinders of filter material of any size and length can be made.

In some embodiments a filter material, such as an electroformed nickel screen or other type of metal screen, is initially made in a square sheet, such as a sheet one meter on each side, and then trimmed to the proper size for the filter. Filter material may be made in larger or smaller sheets depending on the way they are manufactured, for example depending on the available electroforming equipment. The trimmed sheet is flexible and is held in the shape of a cylinder while the seam edges are resistance welded, silver solder or joined by another process known to someone skilled in the art.

In some embodiments, the filter material is coated with one or more materials to provide or improve a desired property. For example, coatings of nickel-phosphorus alloy, chrome alloy or other suitable metal alloys may be used to impart attributes such as hardness and corrosion resistance. In other examples, a filter material may be coated with silver for its antimicrobial properties or a composite containing PTFE for its low friction. In some embodiments, an electroformed nickel screen generally comprises a nickel base and may include one or more additional coatings, such as those described above.

Filter fouling generally occurs in two stages. Initially particles block the pores of the filter material reducing the effective open area. This is simply called "pore blocking." Secondly a layer of particles collects at the filter material surface creating what is called a "cake" layer and this causes an ever decreasing filtrate rate. Crossflow filtration has been shown to be effective in delaying fouling, for example in conjunction with electroformed nickel screens. This mode of operation is generally considered the elegant solution to filter fouling, but the crossflow stream limits the ultimate recovery rate of influent where filtrate is the desired product; and consequently limits the maximum solids concentration in applications, such as filtration of plant biomass.

Surface filters are well suited to be cleaned in place through mechanical means. A number of automated mechanical cleaning technologies may be used, alone or in combination, in various embodiments of the disclosed filter systems and methods. In some embodiments backflushing may be used. In backflushing the forward flow through the filter is entirely stopped and temporarily reversed to dislodge the pore blocking particles as well as the entire cake layer. This backflush liquid containing solids is discarded through an exhaust valve, such as a drain outlet. It is sometimes combined with the operation of a cleaning brush or wiper to aid the cleaning of the filter screen. In other embodiments suction scanning may be used. Here one or more nozzles scan the filter surface. These nozzles have a large suction force causing liquid to flow backward locally through the filter screen in the vicinity of the nozzle. This pulls the filter cake off the screen and sends it to an exhaust valve where it is discarded. In this way a small portion of the filter screen is being cleaned while the rest of the screen continues to operate normally. While general backflush filters have downtime during their cleaning cycle, suction scanning filters continue to operate albeit at a lower net flux rate. As with crossflow filtration, the backflush stream in both systems limits the ultimate recovery rate of influent, and limits the maximum solids concentration.

In some embodiments of the invention described herein, the filter material is cleaned exclusively by use of a wiper. Thus, backflush and/or crossflow are not employed. In other embodiments, the filter material is cleaned by backflush or crossflow. In some embodiments the filter material is cleaned by a wiper in conjunction with a backflush, crossflow or both. Filter screens which have expanding pores and a smooth working surface are well suited to be cleaned by a wiper.

During cleaning the rejected particles move across the surface of the filter material, for example by means of a wiper and/or a crossflow velocity. It is generally advantageous to orient slotted pores of a filter material with their long dimension substantially perpendicular to the likely path of a rejected particle. Thus in some embodiments the filter material comprises slotted pores that are oriented such that the long aspect of the pores is perpendicular to the direction of movement of a wiper.

When a wiper is substantially straight and rotates inside a cylindrical filter, particles move more circularly around the filter than axially down the filter. In this case the slots may be oriented with the axis of filter.

A wiper may also take the form of a spiral in which case the particles may be pushed along a spiral path on the surface of a cylindrical filter. Depending on the pitch of the spiral, the path may be more along the axis of the filter or more along the circumference of the filter. If the filter material comprises slotted pores, the slots can be oriented perpendicular to that path, though a pure axial or circumferential orientation is used in some embodiments, for example due to manufacturing limitations.

Cleaning Assembly—Wipers

A cleaning assembly may be positioned inside the filter assembly and in some embodiments comprises one or more wipers, for example as illustrated in FIG. 2. Fluid may move from the inlet of the housing to contact the inside wall of the filter material by passing around the cleaning assembly, for example as illustrated in FIG. 2, or through the cleaning assembly, for example as illustrated in FIGS. 3 and 4. Filtered particles collect on the inner working surface of the filter and when the cleaning assembly is rotated the wipers clean the working surface of the filter generally by moving filtered particles along the surface and collecting them ahead of the wiper. The wipers may also lift particles off the surface back into the fluid or on to the wipers themselves.

The one or more wipers may be straight or take other useful shapes. In some embodiments the wipers take a substantially spiral shape along the length of the cleaning assembly. See, for example, wipers 316 in FIGS. 3 and 4. In some embodiments the cleaning assembly comprises a single spiral-shaped wiper. In other embodiments, the cleaning assembly comprises two or more spiral shaped wipers. Spiral shaped wipers push particles along the filter surface towards one end of the housing, where they can be collected in a collection region. The concentration of particles on the wiper will typically increase in the direction of the collection region of the housing.

In some embodiments one or more spiral shaped wipers have a fixed pitch and in other embodiments they have a variable pitch. A typical pitch of the spiral wiper, for example for a cylindrical filter that is 4 inches in diameter, would be one complete turn for every 6 inches of cleaning assembly or, in other words, 60 degrees per inch, but could be less or more. In some embodiments the spiral wiper or wipers have a pitch of about 10 to about 360 degrees per inch. Variable pitched wipers have a pitch that changes along the length of the cleaning assembly to accommodate the buildup of particles on the wiper. By way of example, the pitch may change from 10 degrees per inch at the far end of the cleaning assembly to 360 degrees per inch at the end closest to the collection region.

It is generally advantageous to limit the speed of the wipers along the surface of the filter to less than 100 inches per second but this value may be higher or lower depending on the filter and wiper design. In embodiments in which the wiper touches the filter material, friction between the wipers and the filter material causes wear of the wipers, filter material or both. Faster wipers tend to create more turbulence in the unfiltered region of the housing which may interfere with the movement of particles towards the collection region. The wipers may also break particles apart into smaller particles which then pass through the filter material. When the wiper speed is limited, the cleaning frequency on the material can be increased by adding more wipers. A cleaning assembly will typically have from about 1 to about 10 wipers, for example 2, 4, or 8 wipers, but may have more or less.

Wipers may take many forms examples of which are brushes, squeegees and scrapers and may be rigid or flexible. In one embodiment multiple wipers all take the same form and in other embodiments multiple wipers take a combination of forms. Brushes are generally made from non-abrasive plastic fibers like nylon, polypropylene, or polyester, though they may be made from other suitable materials. As particles decrease in size, brushes tend to be less effective and squeegees become more effective. Squeegees may be made from any number of common natural or synthetic rubbers, an example of which is polyurethane. In other embodiments one or more wipers may comprise a scraper. The scraper may be made from any number of suitable plastics such as polycarbonate and PTFE, or other suitable materials.

In some embodiments one or more of the wipers are preloaded against the surface of the filter by deflecting the wiper, such as a brush or squeegee. In other embodiments at least one of the wipers 316 does not touch the surface 214 of the filter but extends to a height slightly above the surface. In some embodiments the wipers may extend to between about 0.001 to 0.1 inches from the surface of the filter, 0.01 inches for example. In this way, circulation of the wipers may create a local crossflow of fluid which tends to push particles along the surface, while the wipers do not actually touch the surface of the filter material.

Figure 10:
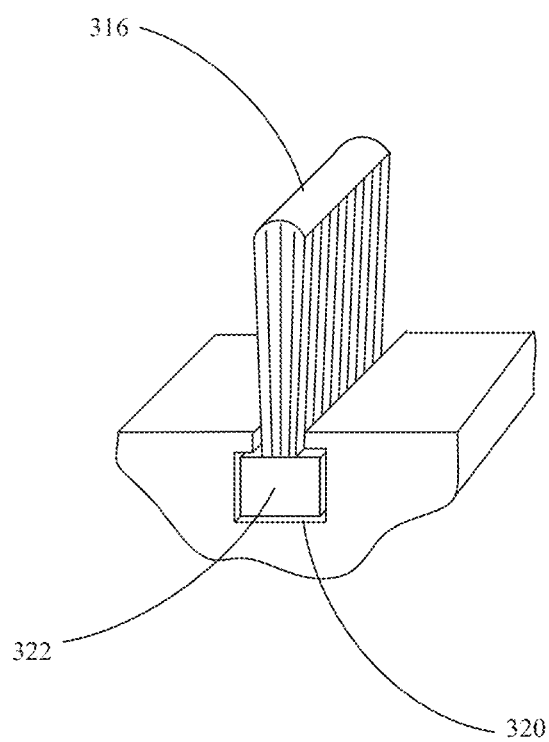
FIG. 10 illustrates a groove on a cleaning assembly which captures the flexible backing of a wiper.

The wipers may be supported by a structure at one or both ends and/or by a center structure as in FIGS. 2, 3 and 4. The center structure may be solid or hollow and take any number of suitable cross sectional shapes, examples of which are round and polygonal. In one embodiment of the invention the center structure is substantially round and has one or more grooves on its exterior surface. As illustrated in FIG. 10, a wiper 316 may have a flexible backing 322 which is inserted into the groove 320 on the center structure. In some embodiments a wiper is glued into a groove 320. In other embodiment the groove 320, as in FIG. 10, has a dovetail or other suitable shape to retain a wiper 316. In one embodiment a wiper is held in place by friction along the length of the groove. In other embodiments a wiper is retained at each end by a plug, end cap, or other suitable means. In other embodiments one or more wipers are glued to a smooth support structure. As mentioned above, in other embodiments the wipers are self-supporting and are not attached to a support structure that runs the length of the wipers. However, they may be supported at one or both ends.

Cleaning Assembly—Distributor

In some embodiments the center structure of the cleaning assembly comprises a hollow tube which can act as a distributor for the filter assembly. The hollow tube is oriented parallel to the length of the filter. The distributor comprises at least one open end which is in fluid communication with an inlet in the housing. For example the distributor may communicate directly with an inlet 101 as in FIG. 4, or may communicate with an inlet region 118 which in turn is in communication with one or more inlets 101 as in FIG. 3.

Figure 11:
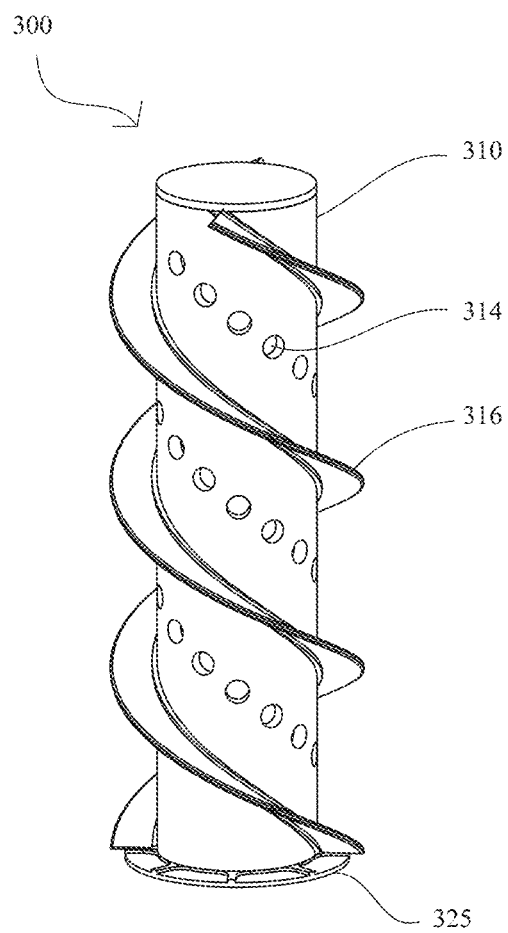
FIG. 11 illustrates an embodiment of the cleaning assembly comprising a distributor with evenly spaced holes arranged in a spiral pattern.

The distributor may extend the entire length of the filter and has one or more openings along its length which distribute the fluid to selected portions of the filter surface. The one or more openings in the distributor may be substantially perpendicular to the length of the distributor. The openings may, for example, be circular holes, for example for ease of manufacturing, but they may also be polygons, slots or any number of suitable shapes. The openings may include tubes or other features which extend outward from the distributor towards the filter surface and direct fluid to the filter surface. A distributor 310 with openings 314 is illustrated in FIG. 11.

In some embodiments, through a rotation of 360 degrees, the distributor can sequentially direct fluid to the entire working surface of the filter. In the embodiment shown in FIG. 11 there are multiple openings 314 which all have the same size. By way of example the openings may be circular holes with a diameter of about 0.25 inches and a center to center spacing of about 0.50 inches along the length of the distributor. In other embodiments multiple openings in the same distributor have different sizes. It is generally advantageous to size the openings in order to balance the amount of flow and pressure being distributed to each selected portion of the filter. Thus the openings may get progressively larger as they get farther away from the inlet and/or the opening in the distributor that is in communication with the inlet. This may take the form of circular holes which get progressively larger in diameter as they get farther away from the inlet in the housing.

In some embodiments the openings point radially outward from the axis of the distributor. In other embodiments the openings are offset from the axis of the distributor and point substantially along a line tangent to the axis of the distributor. Openings which are offset from the axis of the distributor produce flow with a velocity component that is tangential to the filter's surface. In some embodiments of the invention the tangential velocity helps to rotate the cleaning assembly. Additionally, this crossflow may delay fouling and increase performance.

Figure 12:
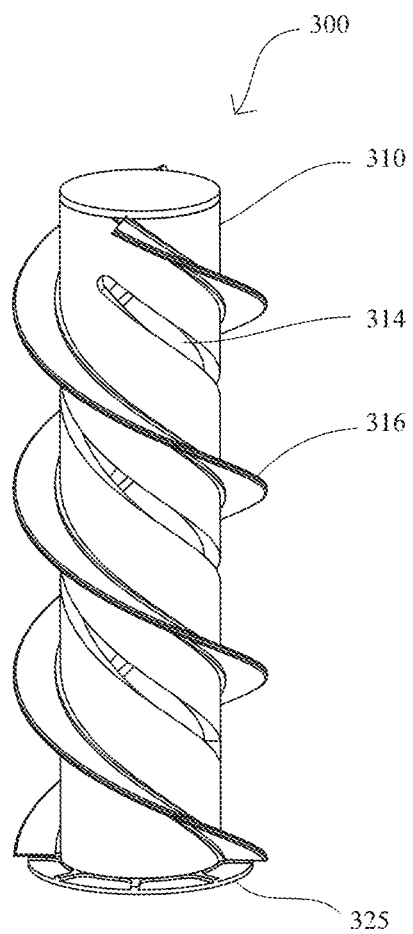
FIG. 12 illustrates an embodiment of the cleaning assembly comprising a distributor with slots arranged in a spiral pattern.

When the cleaning assembly comprises both a distributor and one or more wipers the pattern of openings may match the shape of the wipers. This is illustrated, for example, in FIGS. 11 and 12, where the pattern of openings 314 generally matches the shape of the one or more wipers 316. Thus a spiral shaped wiper 316 will have a spiral pattern of openings 314. In one embodiment the openings 314 are a spiral pattern of holes as shown in FIG. 11, and in another embodiment they are one or more spiral shaped slots as shown in FIG. 12. The size of the openings may vary along the length of the distributor. For example, the slot width may vary along the length of the distributor 310. The slot width may increase with distance from the inlet into the distributor.

When there is more than one wiper, there will generally be a pattern of openings associated with each wiper. The pattern of openings may alternate with the wipers such that each two wipers have a pattern of openings between them.

Cleaning Assembly—Support and Drive

Figure 13:
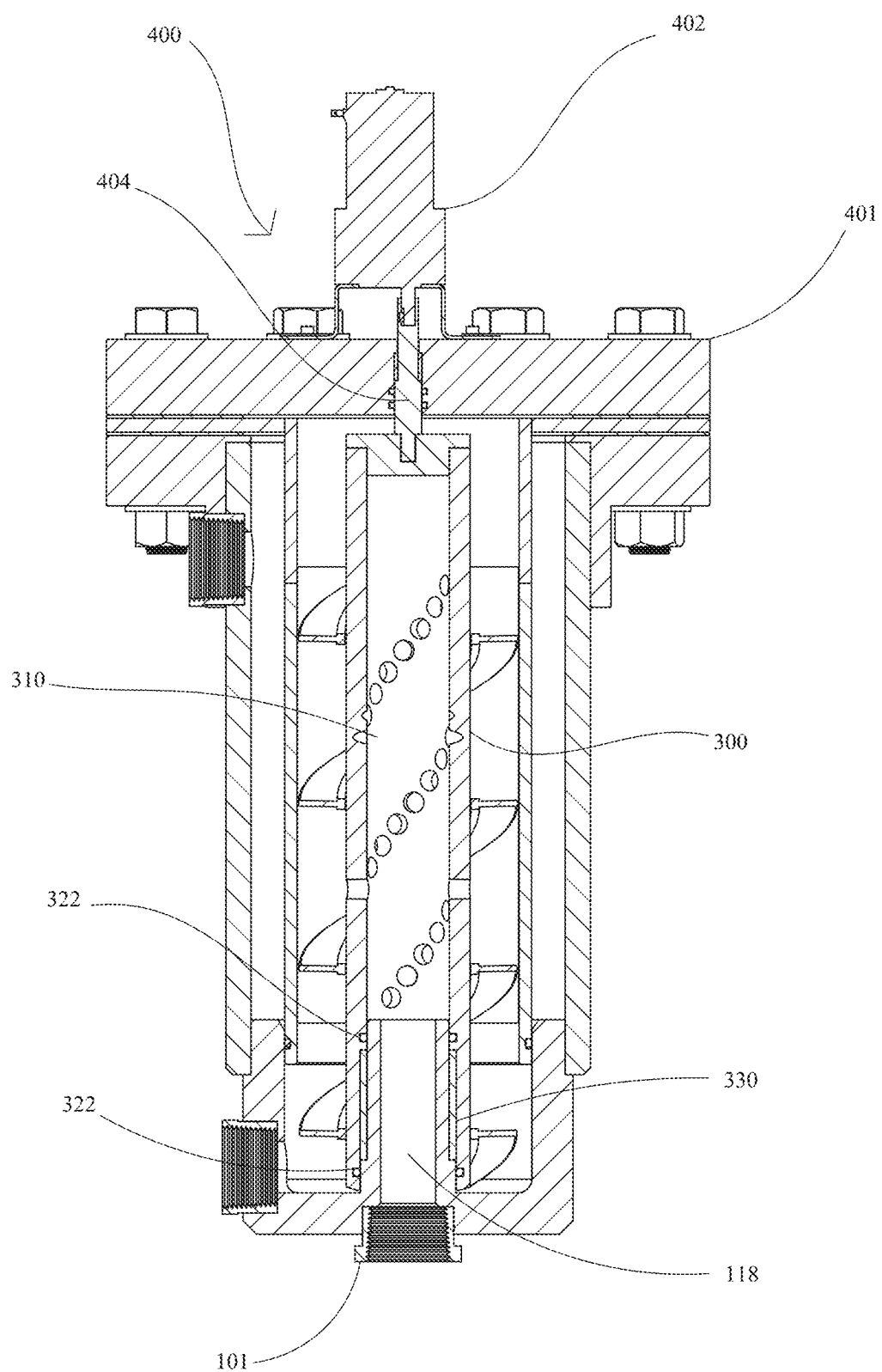
FIG. 13 illustrates an embodiment of the filter system in cutaway showing the cleaning assembly supported by the inlet tube.
Figure 14:
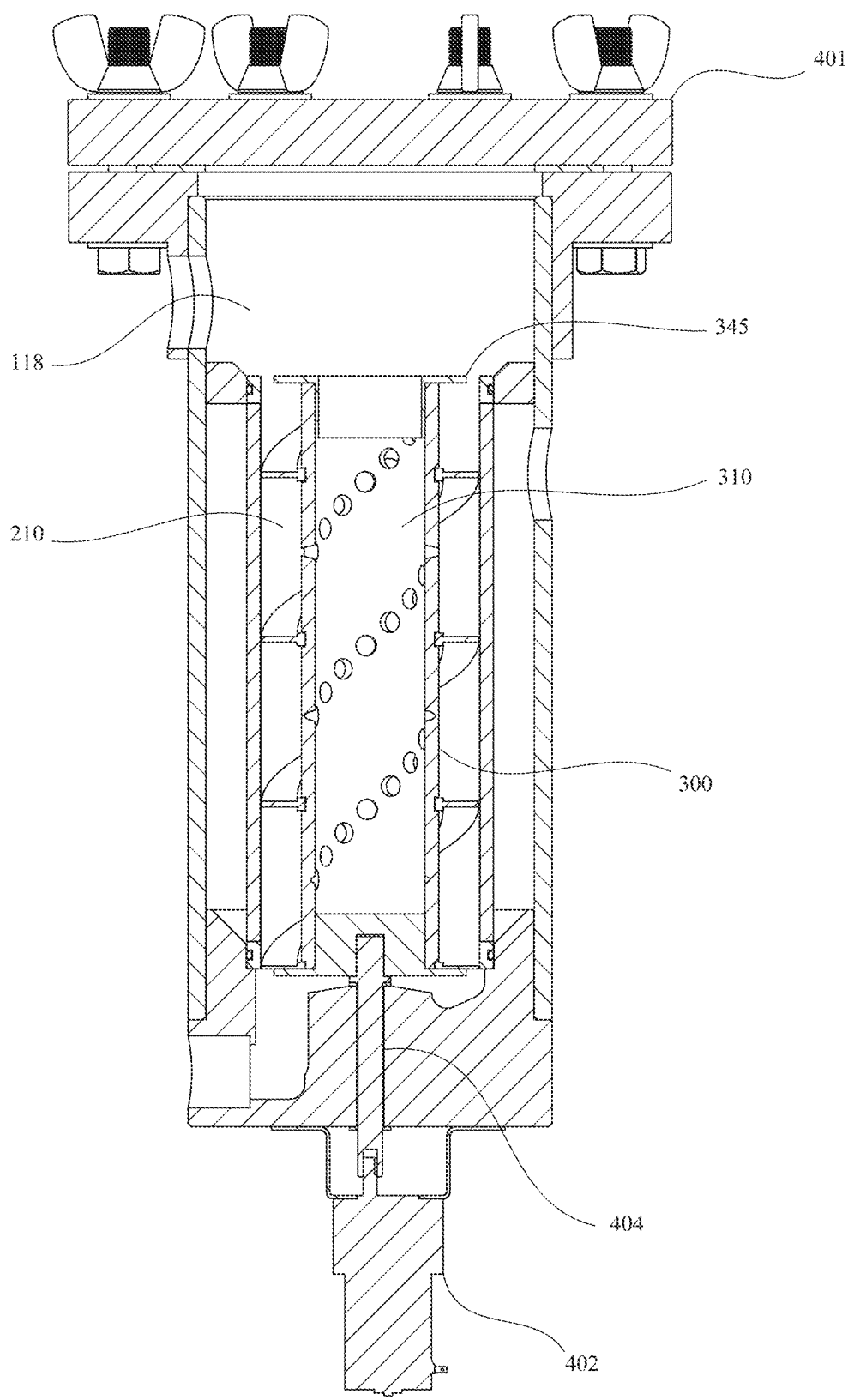
FIG. 14 illustrates an embodiment of the filter system in cutaway showing the cleaning assembly supported by a drive shaft at one end of the housing.

The cleaning assembly may be supported at one or both ends by one or more bearings, examples of which are ball bearings and journal bearings. In the embodiments illustrated in FIG. 4 and FIG. 13, the cleaning assembly 300 is supported by a sleeve bearing 330 on the inlet tube 118 which extends into the housing. One or more seals, such as o-ring seals 322 may also be included to restrict fluid travel around the bearings. A drive shaft 404, which penetrates the lid 401, may also be supported by one or more bearings and sealed by one or more seals. The drive shaft may be coupled to the cleaning assembly 300 using, for example, a spline drive, square drive or interlocking face gears. The lid assembly 400 comprises a motor 402 which couples to the drive shaft 404 and drives the rotation of the cleaning assembly 300. The lid assembly with motor 402 and shaft 404 can be removed from the housing, thus decoupling the shaft 404 from the cleaning assembly 300. In another embodiment the distributor does not get decoupled from the lid assembly but instead gets removed together with the lid assembly. In further embodiments, as illustrated in FIGS. 2 and 3 and further illustrated in FIG. 14, the cleaning assembly is entirely supported by a drive shaft which is supported by bearings and seals at one end of the housing. A motor 402, outside of the housing, couples to the drive shaft 404 and drives the rotation of the cleaning assembly 400.

In even further embodiments the cleaning assembly is driven by other mechanisms, such as by hand or by turbine. A turbine may be located such that fluid flowing into the housing passes through the turbine and turns the cleaning assembly. For example, in the embodiments illustrated in FIGS. 2 and 3 the cleaning assembly may comprise a turbine (not shown) located in the inlet region 118 of the housing. Fluid passing from the inlet region 118 to the distribution region 210 would pass through the turbine driving rotation of the cleaning assembly. In the embodiment illustrated in FIG. 13 a turbine (not shown) may be located inside the distributor 310 such that fluid passing from the inlet tube 118 to the distributor 310 causes rotation of the cleaning assembly 300. In this way no external power source is required to drive the cleaning assembly 300. The power of the flowing fluid may alone provide the drive mechanism.

Cleaning Assembly—Inlet Region Divider

In some embodiments, one or more dividers are used to direct fluid in the housing, such as to direct fluid from the inlet to the distributor. For example, when the cleaning assembly, as in FIG. 14, comprises a distributor 310 which is open at one end to an inlet region 118, it can be advantageous to divide the inlet region 118 from the distribution region 210. In this embodiment a divider 345 protrudes radially outward from the distributor 310 forcing fluid to flow through the distributor to reach the filter. In one embodiment the structure engages the inside wall of the filter assembly or housing through a bearing, seal or both. In another embodiment the divider does not engage the filter assembly or housing and instead allows a small amount of fluid to leak around the divider. In other embodiments the divider is attached to the filter or housing and protrudes inward towards the distributor.

Cleaning Assembly—Collection Region Divider

In some embodiments the rotation of the cleaning assembly drives particles towards one end of the housing where the particles collect in a collection region. The collection region and the cleaning assembly are generally configured to push particles towards the drain outlet. In some embodiments, a divider may separate the inlet region or unfiltered region from the collection region.

When the cleaning assembly comprises a distributor 310, the distributor may not have openings 314 in this region, as in FIG. 3, to avoid turbulence, but may or may not have wipers 316. Wipers 316 in the collection region 116 may be straight, spiral or take other useful shapes and may or may not engage the housing wall. In the embodiment illustrated in FIG. 4 the same wipers which engage the filter continue through the collection region 116 to the end of the housing. In other embodiments additional wipers are arranged on the cleaning assembly to engage the end of the housing.

It can be advantageous to physically divide the collection region from the distribution region to avoid particles returning to the filter surface. In the embodiments illustrated in FIGS. 2 and 3 and those illustrated in FIGS. 11 and 12 this is accomplished by a divider 325 which rotates with the distributor. In other embodiments the divider is non-rotating and instead affixed to the filter wall or housing wall. In further embodiments a rotating divider 325 is used in conjunction with a fixed divider.

Figure 15:
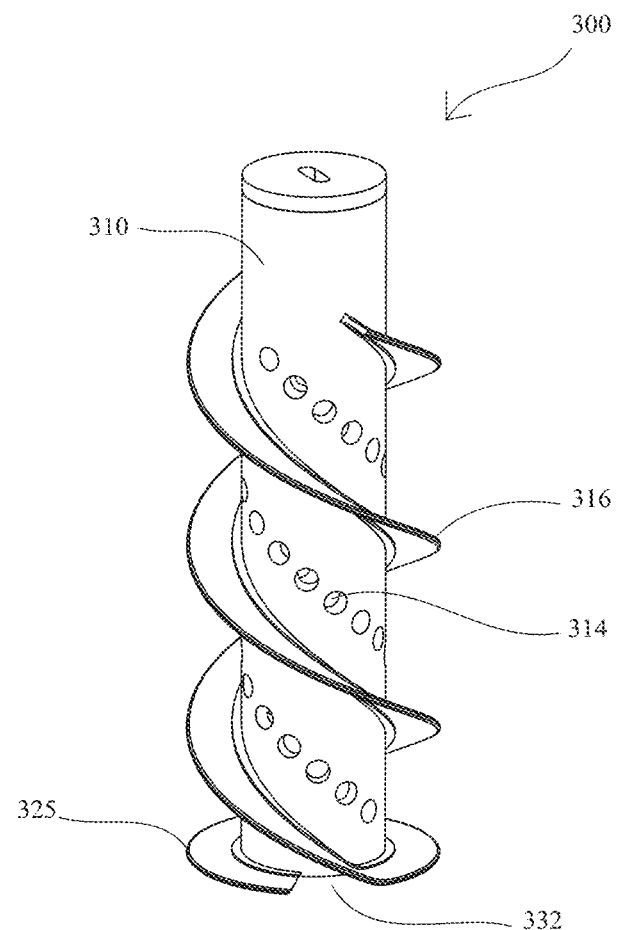
FIG. 15 is an embodiment of the cleaning assembly where the spiral wiper forms a divider which divides the collection region from the distribution region of the housing.

The divider may have one or more openings, generally located adjacent to the filter wall, which are configured to allow particles to easily enter the collection region 116, but to resist particles returning to the unfiltered distribution region 210. Depending on their form, the one or more openings may be fixed or rotating, or a combination of the two. The divider may consist of a flexible wiper like a brush or squeegee, or may take the form of a rigid structure; or a combination of flexible and rigid structures. In the embodiment illustrated in FIG. 15 the divider 325 is formed by a continuation of the cleaning wipers 316 and protrudes from the rotating distributor 310. The wiper wraps around the distributor 310 forming an external arc. An opening 332 is formed by ending the arc before the wiper wraps back around on itself or another wiper.

Cleaning Assembly—Operation

The cleaning assembly may be operated in one or more modes. In some embodiments the cleaning assembly is rotated at a single constant rate whenever a fluid pumping system is turned on. In other embodiments the cleaning assembly is rotated at one of multiple fixed rates depending on the level of filter fouling detected. Fouling of the filter material generally causes reduced flow and increased transmembrane pressure. This can be detected through pressure sensors, flow sensors and others sensors known to someone skilled in the art. By way of example, pressure sensors may take the form of a pressure switch which turns on when a set transmembrane pressure level has been reached. They may also take the form of an electronic pressure transducer which produces an electrical output proportional to the differential pressure across the filter material.

The rotational rate of the cleaning assembly may also be set to be proportional to the solids content of the influent. This can be accomplished using one or more sensors also known to someone skilled in the art, examples of which are turbidity sensors and suspended solids sensors. A still further mode would be to set the rotational rate proportional to the concentration of only those particles likely to cause fouling. This could be accomplished through the use of a particle counter on the influent or a combination of suspended solids sensors at the inlet and filtered outlet. Thus, the filter system may be configured to adjust the rotational speed of the cleaning assembly in response to a signal from one or more of a turbidity sensor, a suspended solids sensor and a particle counter.

The cleaning assembly may contain one or more wipers such that a single rotation of the cleaning assembly will wipe a section of filter material one or more times. The wipers may pass over a section of filter material from once per second up to 20 times per second, but each section of filter material could be wiped less or more often. By way of example, a cleaning assembly having 4 wipers and rotating at 150 RPM would wipe the filter 10 times per second.

Cleaning Assembly—Efficiency

With a surface filter such as those described herein, the retentive force on the pore-blocking particles is created by the transmembrane pressure acting on the area of the particles that is blocking the pore. Fouling may result when the retentive force on the particles is greater than the motive force imparted by the wiper. Different wiper designs will be more or less effective at cleaning particles of different make up. The effectiveness of the wiper can be characterized by a cleaning efficiency factor. The cleaning efficiency for a given wiper design is dependent, in part, on the pore width and transmembrane pressure. The cleaning efficiency generally remains substantially 100% until a critical pressure is reached at which time it quickly drops to 0% as pressure continues to increase. At or above the critical pressure, the wipers are not able to affect pore-blocking particles of ever increasing diameter. Operating beyond the critical transmembrane pressure creates a decaying flux curve, or in other words, the critical transmembrane pressure is the pressure above which the total filtrate rate drops over time. By way of example the critical pressure for a screen with 20 micron wide slots and nylon brushes with 0.006 inch diameter nylon filaments is approximately 3 psi and may be as little as 2 psi or even 1 psi. In one embodiment of the invention the filter system is operated continuously below the critical transmembrane pressure. In another embodiment the filter system operates above the critical pressure, but periodically drops below the critical pressure for a short period of time allowing the wiper to clean the filter. The critical pressure can be determined by monitoring filtration rates at various pressures over time and determining the pressure at which cleaning efficiency drops off to unacceptable levels.

Transmembrane Pressure Regulation

Operation of the filter system to control transmembrane pressure, for example to operate below the critical transmembrane pressure, can be accomplished in a number of ways. In some embodiments the filter system is supplied by a variable speed pump, which is controlled by drive electronics and a differential pressure transducer. The drive electronics change the speed of the pump impeller which varies the flow and pressure output of the pump in order to produce a relatively constant transmembrane pressure.

In other embodiments the filter system is supplied by a single speed pump and additional components are used to regulate the transmembrane pressure. An exemplary filter system along with additional fluid system components is represented schematically in FIG. 16. When the filter system is supplied by a single speed pump 512, the decreased flow of filter fouling causes an increase in the pressure supplied by the pump and subsequently an increased pressure at the unfiltered region of the housing.

Figure 16:
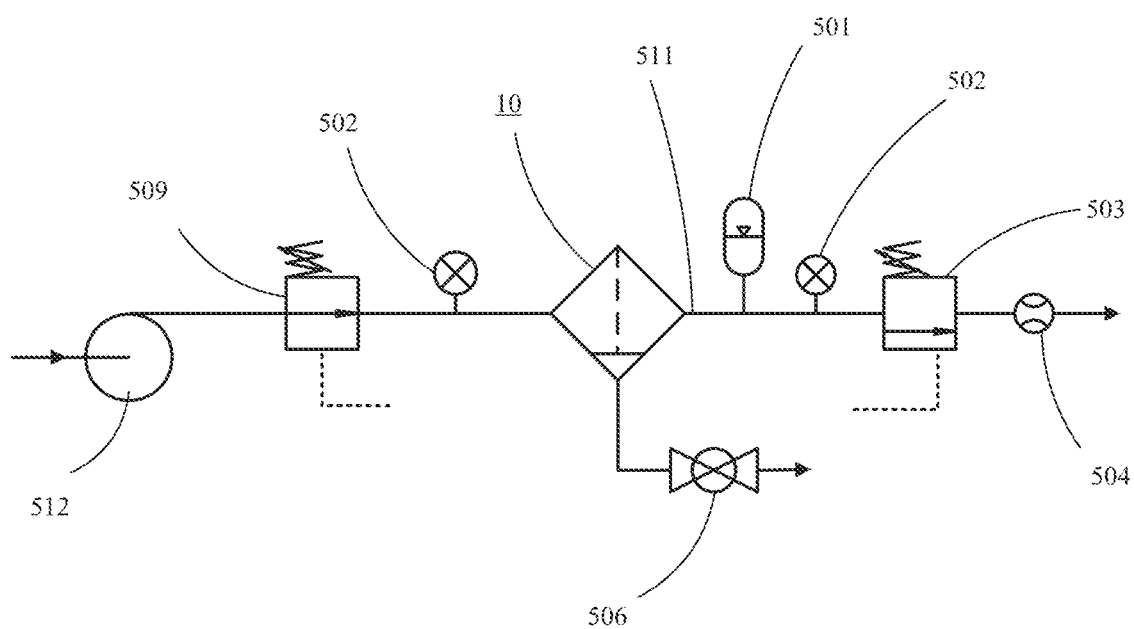
FIG. 16 is a schematic representation of a filter system with an arrangement of various fluid system components that may be used to operate the filter system.

Transmembrane pressure can be maintained by reducing the pressure in the unfiltered region of the housing or increasing pressure on the filtered region of the housing. In one embodiment of the invention flow is restricted at the inlet by a fluid system component 509 thus reducing the pressure at the unfiltered region, as illustrated in FIG. 16. This can be accomplished by a passive regulator, examples of which are pressure regulators and differential pressure regulators; or a flow control valve, examples of which are ball valves and butterfly valves. In another embodiment flow is restricted at the filtered outlet 511 by a fluid system component 503, thus increasing the pressure on the filtered region of the housing. This can be accomplished using a flow control valve or a passive regulator, examples of which are back pressure regulators and differential back pressure regulators.

In some embodiments the transmembrane pressure is maintained with the combination of a pressure regulator at the inlet and a back pressure regulator at the filtered outlet. In some embodiments a differential back pressure regulator is located at the filtered outlet and a pressure regulator is not located at the inlet. In still other embodiments, a differential pressure regulator is located at the inlet and a back pressure regulator is located at the filtered outlet.

In some embodiments flow is increased at the drain outlet 506 using a flow control valve or a pressure release valve. The increased flow through the inlet lowers the pressure supplied by the pump and thus lowers the pressure on the unfiltered region of the housing. In even further embodiments flow restrictors at the outlet are used in conjunction with a pressure source to actively raise the pressure in the filtered region of the housing, thus reducing the pressure differential across the filter material In some embodiments a passive fluid and pressure reservoir 501 is located functionally between the filter material and any regulator 503 at the filtered outlet. This provides a reservoir to equalize the pressure and flow across the filter material when fouling occurs. This reservoir can take the form of an accumulator tank 501 or simply an air bubble trapped in the housing where it can communicate with the filtered region of the housing.

Drain Purge

Particles collected in the collection region may be purged from the housing by one or more methods. In some embodiments, the pump supplying the system is turned off and the drain valve is opened. The particles and fluid in the housing then simply drain out. This could be useful, for example, for swimming pools and other consumer applications where cost is an issue and routine maintenance is expected. In other embodiments the drain valve is fully opened while the pump continues running. This flushes the collection region while also causing a sudden drop in pressure in the unfiltered region of the housing. The drop in pressure can help to unclog any pores which might be retaining particles. When a pressure and fluid reservoir exists at the filtered outlet a small amount of fluid may flow backwards through the pores of the filter further helping to dislodge stuck particles. This passive back flush can be further aided by simultaneously closing a valve that is positioned at the filtered outlet after the pressure reservoir, such as valve 503 in FIG. 16.

In further embodiments the filter system is operated while the drain remains only slightly open. A small fraction of the fluid, generally in the range of 1% to 10%, passes out through the drain taking with it the rejected particles. A continuous drain of this nature is often called a bypass flow or a brine stream.

In even further embodiments the system is operated as a crossflow filter. In such a configuration a certain amount of flow passes out through the drain and creates a flow velocity tangential to the surface of the filter. This tangential flow acts as a cleaning mechanism which can work by itself or in conjunction with the wipers to reduce or eliminate fouling. In crossflow applications the bypass flow is optimally run at about 50% but can range from about 10% to 90%. In some embodiments the bypass flow makes a single pass through the filter system. In other embodiments the bypass flow is pumped back into the system and makes multiple passes through the filter.

It is also possible to purge particles from the system without substantially impacting the pressure or flow of the system. Some embodiments use a rotary valve located at the drain outlet. In some embodiments a valve element comprises one or more cavities which can be opened sequentially first to the collection region and then to the drain by the rotation of the valve element. In some embodiments a valve element comprises a positive displacement pump. In some embodiments a seal around the valve element maintains the pressure in the collection region. The rotary valve and/or positive displacement pump can be driven by a motor or by hand. In one embodiment the element is coupled to the distributor and driven simultaneously. If coupled to the distributor it may be coupled through one or more gears to reduce the rotational speed of the valve with respect to the distributor. A typical gear ratio would be 1:100 but could be as low as 1:10,000 or as high as 1:1.

In one embodiment a valve is operated in a continuous fashion whenever the filter is in operation. In other embodiments one or more sensors or switches operates the valve. The valve can be operated by a timer; in response to filter fouling; or in response to solids accumulation in the collection region. Filter fouling can be indicated by an increased pressure differential or decreased flow which can be detected by pressure and flow sensors. Solids accumulation can be detected by a variety of sensors, examples of which are optical sensors and acoustic sensors. In one embodiment the valve is a separate unit attached to the drain outlet. In other embodiments the valve is integrated into the end or side wall of the housing.

Housing Design

Figure 17:
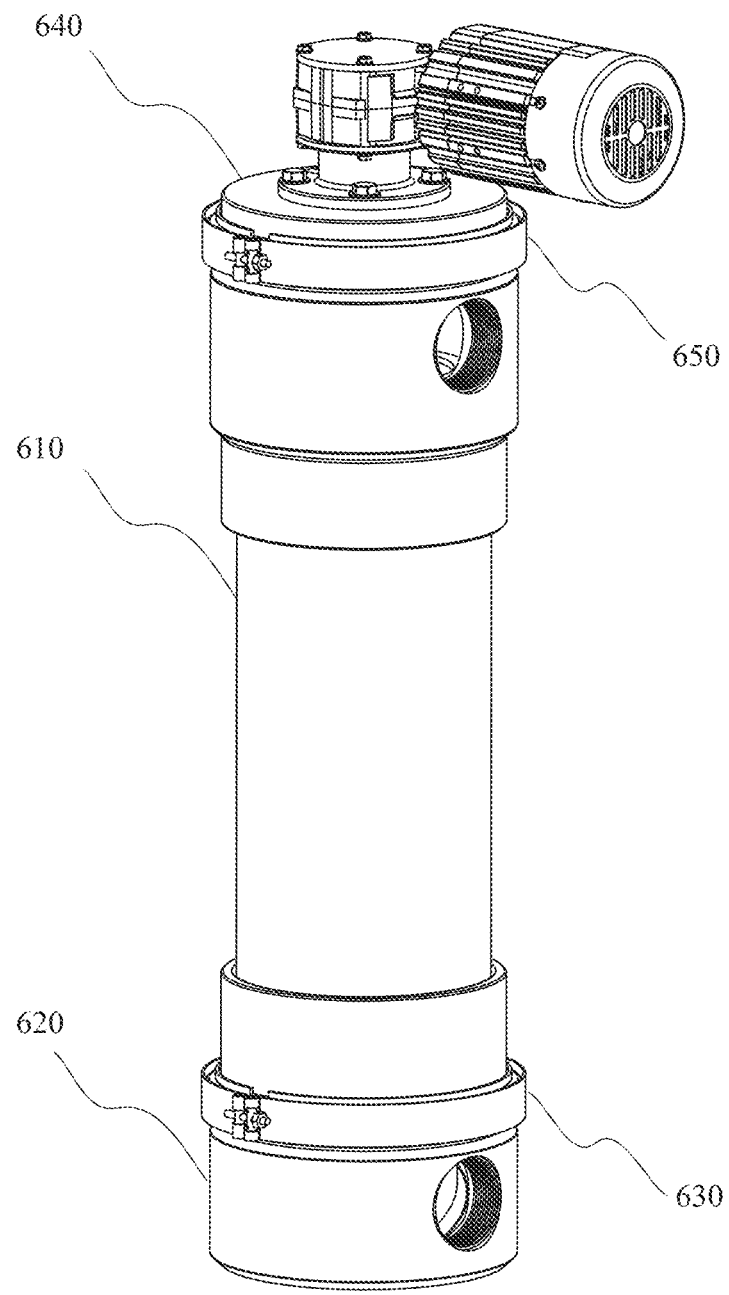
FIG. 17 illustrates an embodiment comprising an inlet housing, an outlet housing and a lid.
Figure 20:
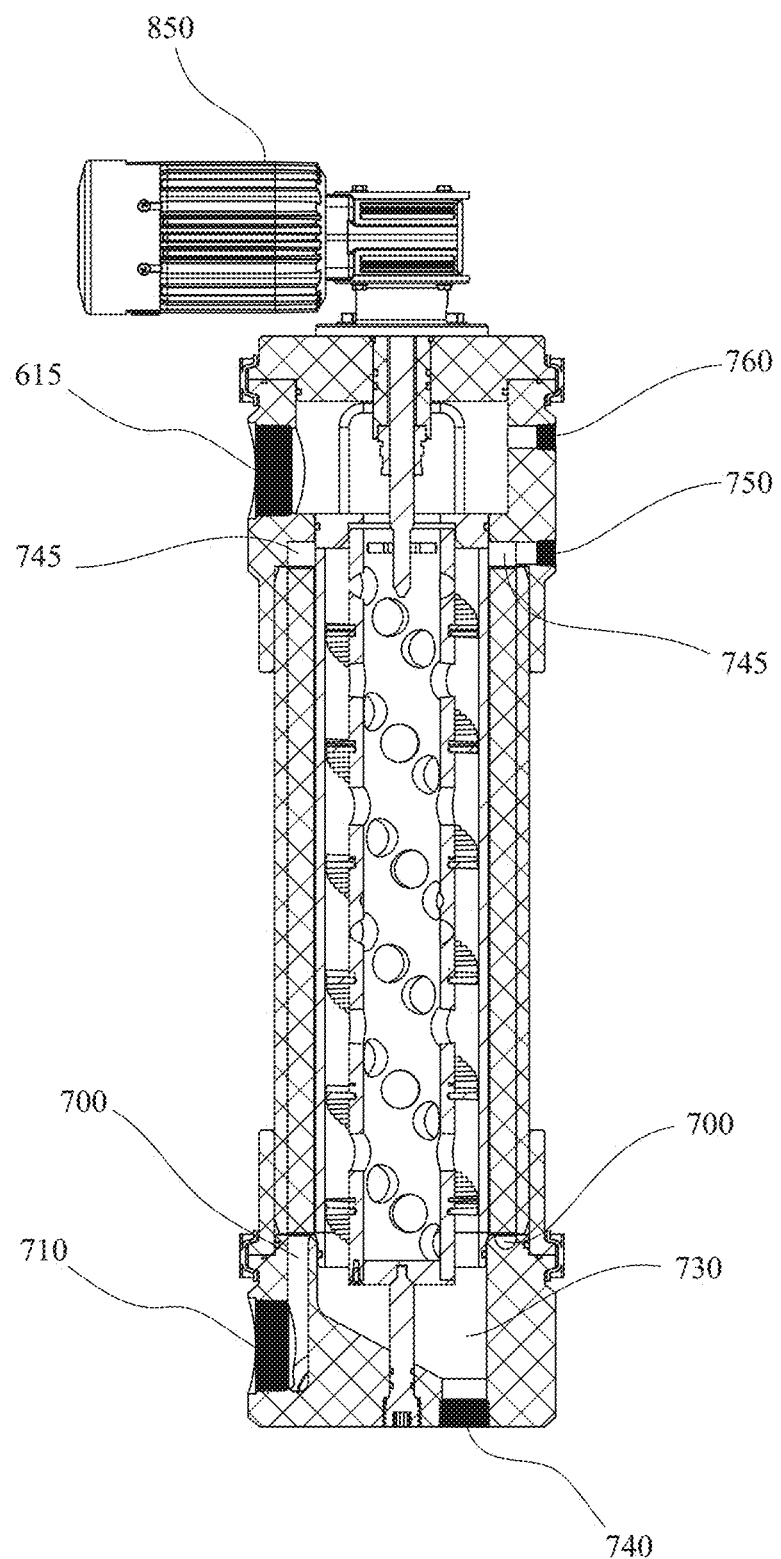
FIG. 20 illustrates an embodiment of a filtration device in cutaway view.
Figure 21:
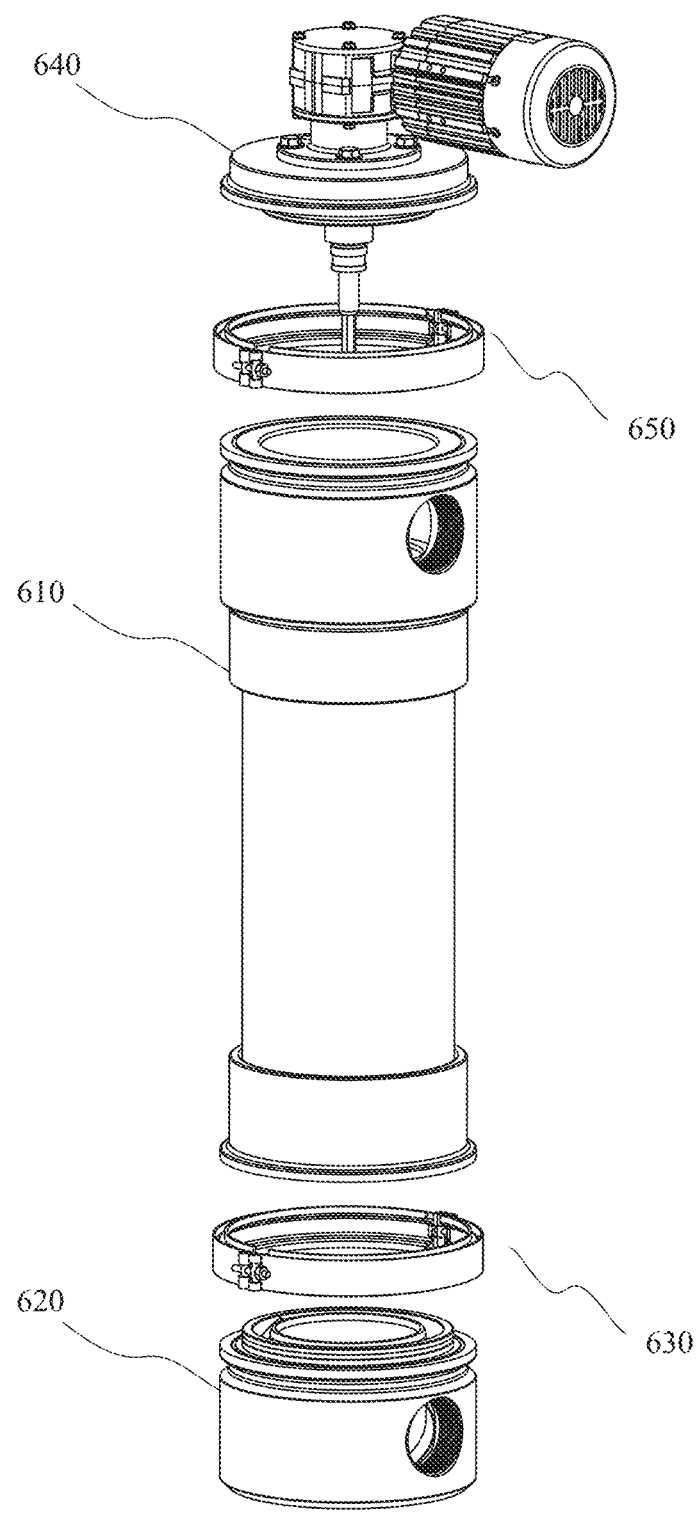
FIG. 21 illustrates a housing in exploded view.
Figure 22:
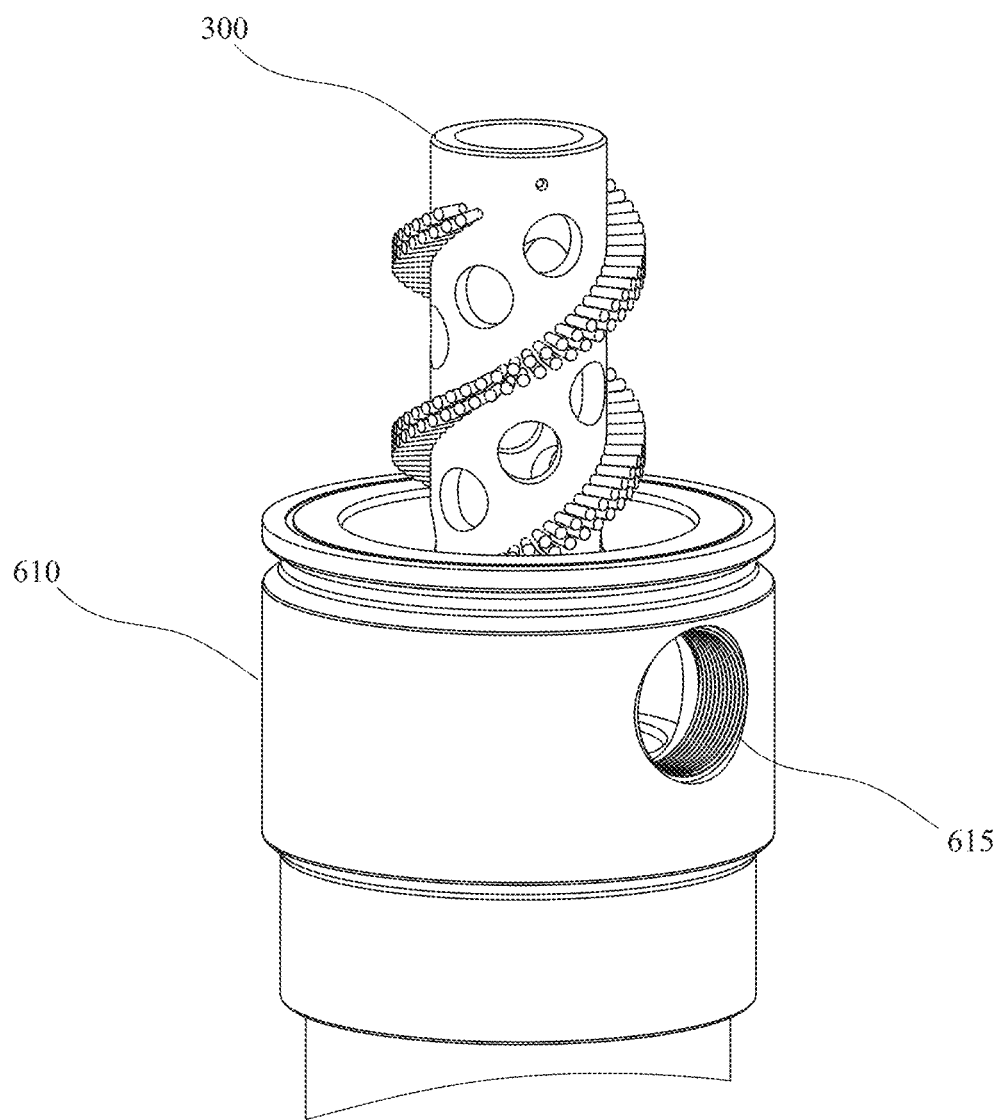
FIG. 22 shows insertion of a cleaning assembly into a housing.
Figure 23:
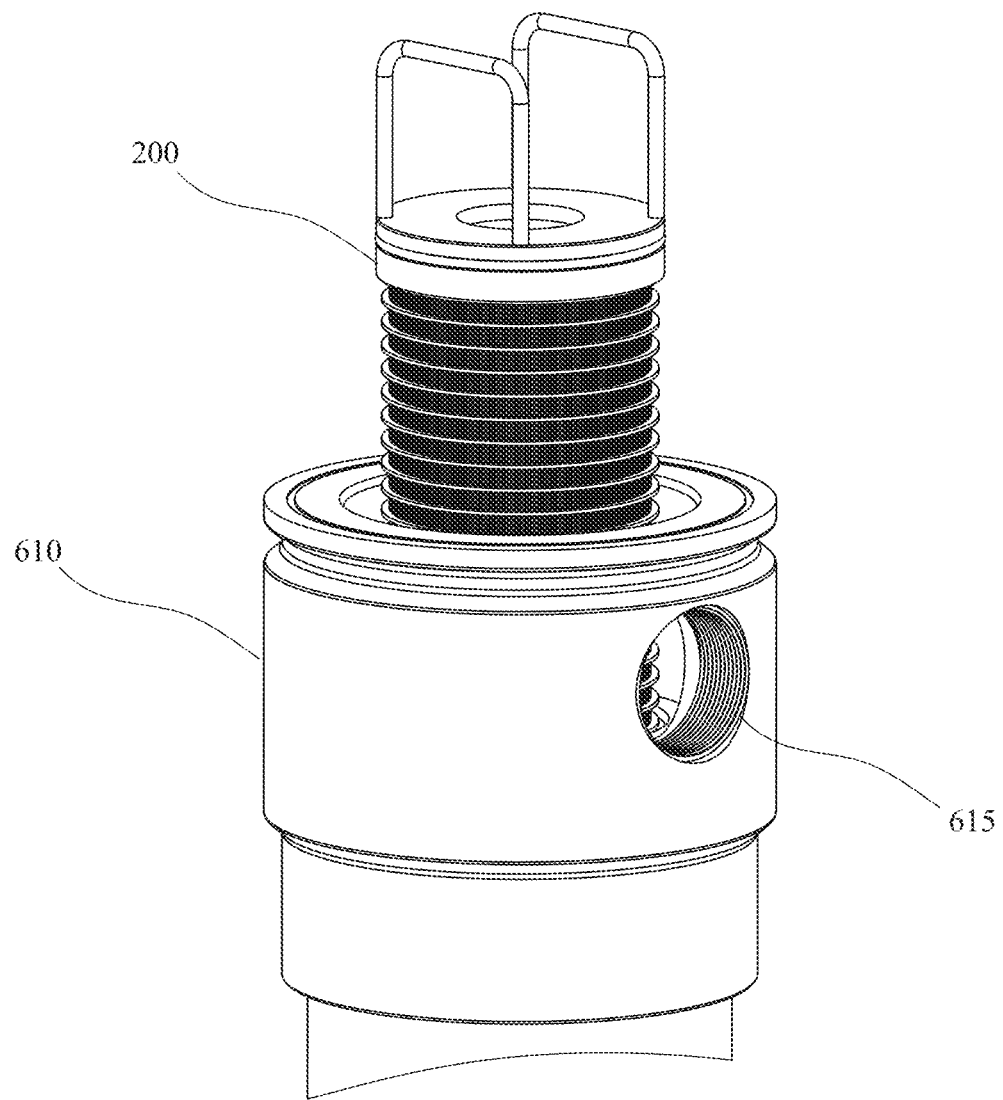
FIG. 23 shows a filter being inserted into a housing.
Figure 25:
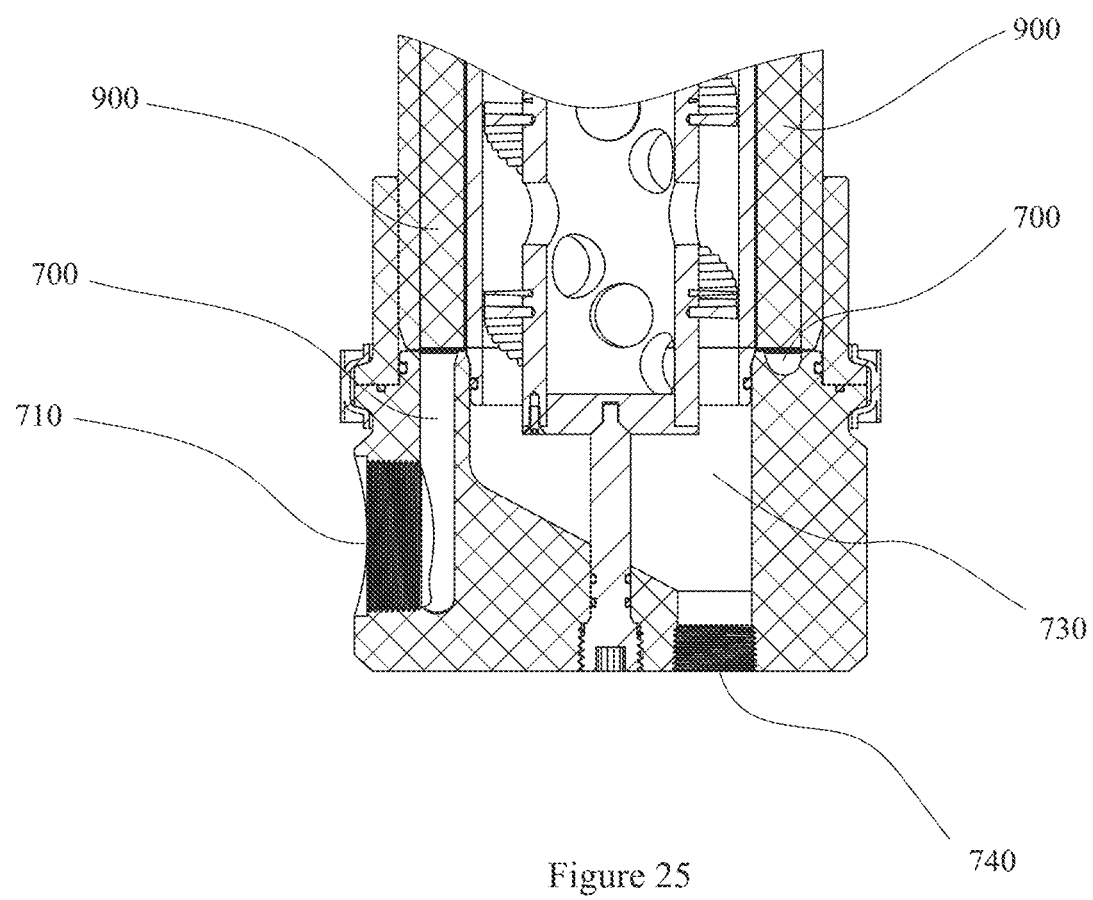
FIG. 25 shows a cutaway view of a housing filter and cleaning assembly.

In some embodiments, for example as illustrated in FIG. 17, a housing comprises an inlet housing 610 and an outlet housing 620. The two separate inlet and outlet housing parts 610, 620 may be joined, for example by a band clamp 630 and may be sealed, for example with O-Rings, as illustrated in FIG. 21, but may be joined and sealed in any number of other ways. The housing may further comprise a lid 640 which is joined to the inlet housing, such as by a band clamp 650 and O-Rings, but may also be joined and sealed in any number of suitable ways. As illustrated in FIGS. 22 and 23, the inlet housing may include one or more inlets 615 which communicate with the inside of the filter, for example as discussed elsewhere herein. FIG. 22 also illustrates how the distributor 300 is disposed inside the inlet housing and FIG. 23 illustrates the filter assembly. As illustrated in FIGS. 20 and 25, in some embodiments the outlet housing comprises a filtered region 700 and filtered outlet 710, which communicates with the filtered region of the inlet housing. In some embodiments the outlet housing additionally comprises a drain region 730 and drain outlet 740, which communicates with the unfiltered inside of the filter.

Cleaning Assembly

Figure 18:
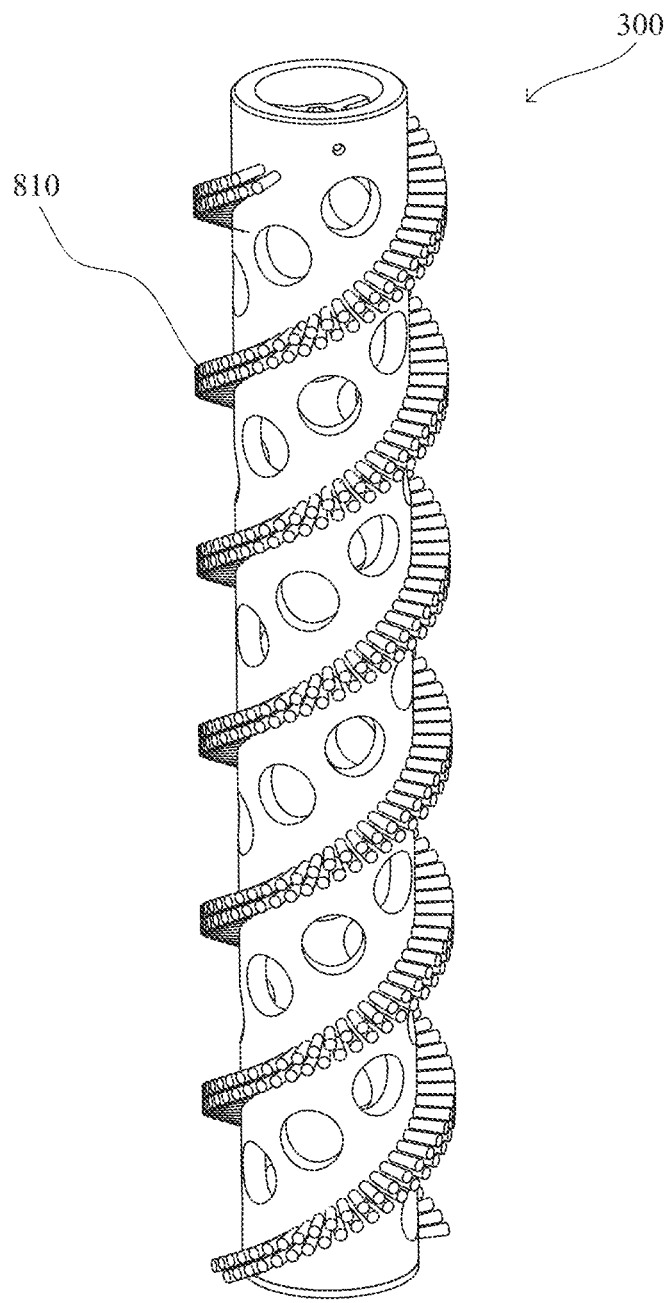
FIG. 18 illustrates an embodiment of the cleaning assembly.
Figure 19:
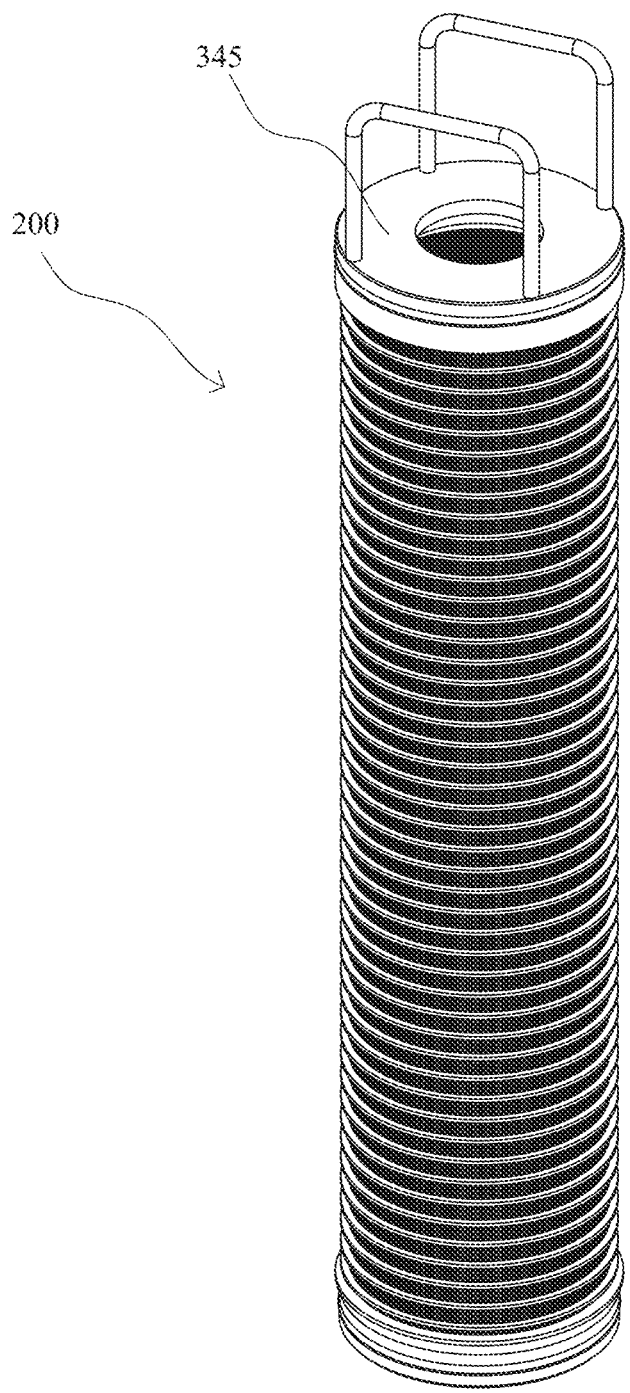
FIG. 19 illustrates an embodiment of the filter assembly.

The rotating cleaning assembly 300 may comprise a spiral shaped wiper and hollow support structure. In some embodiments the wiper comprises brush filaments and in one embodiment the brush filaments 810 protrude outward from the support structure in bunches, as in FIG. 18. Each bunch may be affixed into holes which are drilled in the support structure. In one embodiment each bunch is joined to the support structure using a staple. The pattern of bunches may comprise a single row or multiple rows of bunches taking a spiral pattern or other suitable shape. In the embodiment of FIG. 18 the cleaning assembly comprises a distributor and wiper but no dividers. In this embodiment the inlet region divider 345 is stationary and located on the filter assembly 200 as shown in FIG. 19. In some embodiments the filter assembly 200 comprises a wedge wire screen and metal end caps. The outlet region divider may be stationary and located on the outlet housing or may not be present as shown in FIGS. 20 and 25. In the embodiment illustrated in FIG. 20 the cleaning assembly is driven by a motor 850 that is mounted to the lid and coupled by a drive shaft. The cleaning assembly is additionally supported by a pin that is coupled to the outlet housing.

Baffles and Other Flow Regulators

Fluid generally passes from inside of the filter to the outside of the filter, after which it is undesirable for the fluid to flow back to the inside of the filter. However, in some situations this backflow may occur in certain areas of the filter and particulates may accumulate on the outside of the filter. For example, backflow may cause the outside of the filter to plug up with particulate in some areas. Since the cleaning assembly does not generally make contact with the outside of the filter, this can cause premature fouling. Besides backflow there may be other undesirable fluid dynamics that may sometimes occur between the outside of the filter and the housing, another example of which is stagnation zones. Regions of fluid may become stagnant in places such as near housing walls, near internal corners and in regions where fluid paths separate. A stagnation zone can cause particulate to settle out of the fluid stream and collect in the housing. These solids can obstruct flow and if they grow to a certain size may even plug the filter from the outside. A further example of undesirable fluid dynamics is uneven flow across the filter screen. It is generally desirable to maintain equal flow across the entire surface of the filter. In this way one part of the filter does not wear or plug any quicker than other parts of the filter.

The undesirable fluid dynamics, described above, may be at least partially alleviated by the addition of one or more flow-directing features that direct the flow of filtered fluid between the outside of the filter and inside of the housing. In some embodiments the flow directing features are used without a cleaning assembly inside the filter, for example with disposable bag or cartridge filters, or with self-cleaning filters like backflushing filters. In other embodiments a cleaning assembly is additionally located inside the filter. In some embodiments the cleaning assembly is a rotating cleaning assembly, but may take other forms. In one embodiment the cleaning assembly comprises a rotating distributor and one or more wipers. In some embodiments the flow directing features comprise one or more channels located between the housing and the filter assembly. In some embodiments flow-directing features comprise baffles 900, for example as pictured in FIG. 24, which extend from the inside of the housing 910 to the outside of the filter assembly 920, or vice versa, thereby creating one or more channels 930 that direct fluid passing through the filter toward the outlet region 700 as illustrated in FIG. 25. In some embodiments channels may be formed or created in the housing itself. The housing, or at least the channel forming portion of the housing, may be adjacent to or contacting the filter, such that fluid passing through the filter is directed by the channels toward the filtered outlet. In some embodiments channels may be formed or created in the filter assembly itself. For example, the filter assembly may comprise material that supports the filter while forming channels at intervals down at least a portion of the length, as illustrated in FIG. 5. In some embodiments the portion of the filter assembly that forms the channels contacts or is closely adjacent to the housing.

In some embodiments one or more channels extend the entire length of the filter, while in some embodiments they extend a portion of the length of the filter, for example half of the length of the filter or more. In some embodiments one or more channels begins at the top of the filter. In some embodiments, as illustrated in FIG. 20, the channels begin below the top of the filter, for example 1 inch below the top of the filter. The region 745 above the channels allows each and every channel in the filtered region of the housing to communicate with an air release outlet 750. In some embodiments the unfiltered region may additionally communicate with an air release outlet 760.

In some embodiments one or more baffles 900 extend the entire length of the filter. In some embodiments the one or more baffles extend a portion of the length of the filter. For example, in some embodiments two or more baffles begin at the top of the filter (closest to the inlet) and extend the entire length of the filter. In some embodiments two or more baffles begin at the top of the filter and run at least half way down the length of the filter.

Figure 24:
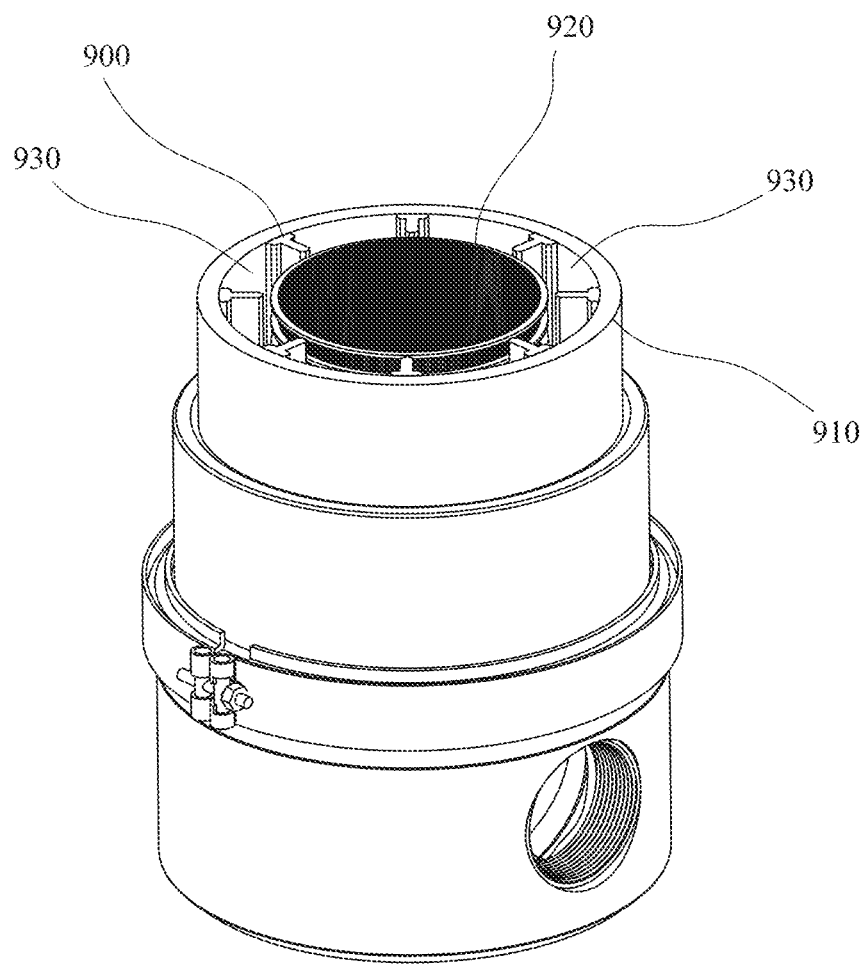
FIG. 24 illustrates an embodiment of a housing comprising baffles.

In some embodiments, as illustrated in FIG. 24, the baffles are affixed to the housing and extend toward the filter. This configuration of baffles may also facilitate insertion of the filter assembly into the housing, as the baffles align the filter in the center of the housing. This may be especially advantageous with very long filters when the housing is mounted in a horizontal orientation. In some embodiments the baffles may be affixed to the filter assembly and extend toward the housing. Such a configuration may also serve to align the filter in the center of the housing.

In some embodiments baffles extend the entire distance between the filter and the housing, such that fluid movement is restricted to a channel. In other embodiments one or more baffles may extend only part of the way between the filter and the housing, such that they direct the fluid but fluid movement past the baffles, such as between channels, is possible.

When baffles are present it is generally advantageous to locate the filtered outlet at one side of the housing beyond where the baffles are located, though in some embodiments the outlet is located in the baffled area. Baffles may be attached to the filter and/or filter assembly and extend outward or may attach to the housing and extend inward, or may be attached on both sides to both the filter and the housing. In one embodiment the baffles and housing together consist of a single extrusion of material, and in other embodiments the baffles are individually, or in groups, bonded, welded or otherwise affixed to the housing wall. They may extend the entire distance between the filter and housing or they may extend only part of the way. Any number of baffles may be used. In the embodiment illustrated in FIG. 24 there are 8 baffles 900. Other embodiments may have 2, 3, 6, 10 or other numbers of baffles. The baffles may all be evenly spaced or have uneven spacing. In some embodiments the baffles are parallel and run along the axis of the housing. In other embodiments the baffles may not be parallel and may have other advantageous configurations.

Channels 930 are created by adjacent baffles. These channels generally keep the flow of the fluid all moving in one direction. For example, fluid that has passed through the filter material may enter the channels and be directed toward the outlet region and the filtered outlet. The baffles may reduce the occurrence of vortices and stagnation zones which can cause backflow and particulate settling.

The material, thickness and shape of the baffles may be selected to achieve the desired channel size and/or to provide specific flow direction and/or behavior. In some embodiments each channel has a consistent cross section along its length, for example along the length of the filter housing. This may be achieved, for example, by selecting baffles that are essentially parallel and of uniform size along their length. More fluid is generally flowing in the channel as the flow gets closer to the outlet. In channels where the cross section remains consistent, the fluid velocity increases as more flow enters the channel. In other embodiments the cross section of each channel may change size and/or shape at one or more points along its length, such as along the length of the housing. In one embodiment the channels have a cross section that gets larger as the flow gets closer to the outlet. For example, this may be achieved by baffles that decrease in thickness at one or more points along their length, by changing the thickness of the housing wall at one or more points, and/or by changing the thickness of the filter assembly material, such as toward the bottom of the housing. In some channels the shape and spacing of the channels is selected such that the fluid velocity may remain generally consistent through the length of the channel.

The channels may include other flow modifying features that influence the flow of fluid as it passes from the filter to the filtered outlet. In some embodiments these flow modifying features may help keep solids suspended and/or prevent backflow. In some embodiments one or more of the surfaces of one or more channel may comprise one or more flow modifying features. For example, the housing wall and/or the surface of the baffles may not be smooth. In some embodiments one or more surfaces that form a channel may have bumps, ridges or divots. These features tend to create turbulent flow which may prevent the settling of solids.

Wiper Design

The cleaning efficiency of the wiper may be dependent on the speed of the wiper along the working surface of the filter, but it may also be dependent on other variables. In some embodiments it is advantageous to limit the speed of the wiper. In some embodiments of the invention the cleaning assembly rotates intermittently. This can be done using a fixed interval of rotation and non-rotation. Rotation can also be triggered by an event such as a buildup of differential pressure across the filter element. In other embodiments it is advantageous to maximize the speed of the wiper. As described earlier the speed of the wiper along the surface of the filter may be limited to less than 100 inches per second. It may also be higher or lower depending on the filter and wiper design.

In some embodiments of the invention the wiper pushes particles along the surface of the filter by touching the particles. In other embodiments the wiper creates a pumping force to push particles along the surface of the filter. The wiper may act like the impeller blades of a pump. The pumping force may take the form of a pressure gradient. It may also take the form of a hydrodynamic force, for example a vortex or drag force. A rotating cleaning assembly may act like a centrifugal pump, a screw pump, another rotating pump, or a combination of pumps. In some embodiments of the invention the cleaning assembly produces a cleaning force on the particles which does not change with respect to the rotational rate of the cleaning assembly. In other embodiments the cleaning force is proportional to the rotational rate of the cleaning assembly. In further embodiments the cleaning force is proportional to the square of the rotational rate of the cleaning assembly. In even further embodiments other relationships may exist between the force on the particles and the rotational rate of the cleaning assembly.

The relationship between rotational rate of the cleaning assembly and the cleaning force may be different in different regimes. For example a cleaning assembly may act like a wiper at one speed and a pump at higher speeds. To further illustrate this point, the cleaning assembly may act like a wiper between 1 and 60 RPM, and like a pump at speeds greater than 60 RPM, for example 100, 300 or 700 RPM.

In one embodiment of the invention the cleaning assembly has a wiper and the rotating wiper produces a pumping force towards one end of the cylindrical filter element. The pumping or cleaning force created by the wiper acts on the solid particles which are retained by the filter element, while the flow through the filter creates a resistive force on the particles. The cleaning force is proportional to the square of the rotational speed of the cleaning assembly, while the resistive force on the particles is proportional to the flow rate through the filter element and inversely proportional to the open area of the filter element. To avoid fouling the filter, the cleaning force must be larger than the resistive force. Thus the flow rate through the filter is limited by the rotational rate of the cleaning assembly. By spinning the cleaning assembly twice as fast, 4 times the flow may pass through a given filter element, for a fixed open area. In one embodiment of the invention the cleaning assembly comprises two spiral shaped wipers an outer diameter of approximately 4 inches. The wipers are mounted to a distributor having an inner diameter 2 inches and a wall thickness of 0.375 inches. The wipers have a pitch of 6 inches per turn. A cleaning assembly that is 18 inches long rotates inside a filter element that is 18 inches long and 4 inches in diameter. The cleaning assembly rotates at between 100 and 800 RPM, but can be higher or lower.

Solids Sensing Technology

The torque required to rotate the cleaning assembly may be dependent on a number of variables including but not limited to the flow rate of liquid through the filter, the viscosity of the unfiltered fluid and the amount of solids accumulated in the filter housing. In one embodiment of the invention a measurement of the torque required to spin the cleaning assembly is used to measure the viscosity of the unfiltered fluid. In another embodiment the torque measurement is used to measure the amount of solids accumulated in the filter housing. And when a sufficient amount of solids have accumulated in the filter housing, the torque measurement may be used to trigger the purge valve to open.

In an embodiment of the invention the torque may be measured by means of a torque sensor. In another embodiment the cleaning assembly is driven by an electric motor and the torque is related to the electric current used by the motor. The electric motor may be of the brushed DC type, brushless DC, 3-phase AC, single phase AC or some other type of electric motor. The current may be measured by way of a current sensor, a current switch or other sensor known to someone skilled in the art. In one embodiment the motor is a 3-phase electric motor, driven by a variable frequency drive (VFD) and the VFD monitors the current. The VFD provides a digital signal indicating when the purge valve should open. The VFD may also provide an analog signal indicating the level of solids in the housing or the viscosity of the fluid.

In some embodiments the cleaning assembly torque is used to measure the viscosity of the fluid being filtered. Viscosity can be related to the type of fluid. It can also be related to the solids content of the fluid. Higher solids content is generally associated with higher viscosity. In some industrial processes the viscosity of the fluid can be used to measure the quality of the process. For example in the paint and coatings industry, the viscosity of the product is extremely important. In wastewater applications the viscosity of the wastewater can be related to the solids content of the wastewater. Knowledge of the solids content can be used to monitor the output of a plant. This can be important in the food and beverage industry as well as other industries. In some embodiments the fluid comprises plant biomass and the solids content of the fluid is measure by measuring the torque on the cleaning assembly.

In some embodiments the cleaning assembly has one or more wipers and the movement of the wiper(s) through the fluid creates a resistive force which can be measure by the torque on the cleaning assembly. The wipers may extend down into the purge chamber to measure the solids content of the purge chamber. In other embodiments the cleaning assembly has a separate structure which moves through the fluid to create a torque on the cleaning assembly. The cleaning assembly may have a structure which projects beyond the length of the filter down into the purge chamber. The rotation of this structure in the purge chamber produces a torque on the cleaning assembly and higher torque equates to greater solids content in the purge chamber. The structure may take the form of one or more rods, bars or tubes. It may also resemble an egg-beater or mixer. In some embodiments the rotating structure or wiper keeps the solids from settling.

Settled solids may create a build-up or cake which cannot be purged through the purge valve.

Plant Part Filtration

Plants often comprise structures that contain useful compounds. For example, some plants comprise small structures on the surface that contain useful compounds, such as trichomes and lupulins. It is desirable to be able to separate these small structures from other plant biomass to facilitate extraction of the desired components. Trichomes may be found on the leaves, stems and flowers of various plants. A common type of trichome resembles a hair. Other trichomes may resemble scales. Plant trichomes may be glandular, producing a compound useful for the plant. Often times chemicals produced in the trichomes are also desired by humans for various purposes. The cannabis and hemp plants comprise trichomes that produce useful chemicals called cannabinoids and terpenes. Useful cannabinoids include such chemicals as THC and CBD. There are other plant structures which also produce useful compounds. For example, the lupulin is a glandular hair found on the hop plant and contains compounds useful in beer making. In some embodiments one or more plant parts are separated from other plant biomass by filtration through a filtration apparatus as described herein.

Once the desired plant parts have been collected, they may be further processed to obtain the desired components. For example, the active compounds manufactured in plant structures like trichomes and lupulins may be extracted and isolated. Methods of extracting and isolating compounds from plant structures include the use of heat and/or pressure to force the desired compounds out of the structures. Other methods use solvents to extract the desired compounds. Examples of these methods include ethanol extraction, butane extraction and supercritical $CO_2$ extraction. Many extraction methods may be performed on raw plant material, but in many situations it is more efficient if they may also be performed on structures, like trichomes or lupulins, after the trichomes or lupulins have been separated from other plant material. For example, the mass of trichomes or lupulins is a fraction of the entire plant mass, for example from about 1% to 20% of the total plant mass. Extraction methods are much more efficient when performed on separated and concentrated trichomes or lupulins that have been separated from other plant biomass, rather than on the entire plant biomass.

In order to scale up separation of desirable plant parts such as trichomes or lupulins to industrial levels, automated processes would be beneficial. Automated filter technologies, for example backflushing filters, have not been used because they cannot handle high solids concentrations without plugging up, nor can they concentrate solids. The filtration device and methods described herein are well suited to isolate and concentrate trichomes. It was unexpectedly found that the filtration apparatus and methods described herein could be used to efficiently isolate plant structures such as trichomes and lupulins. These findings were unexpected because automatic filter technologies generally cannot handle influent concentrations of solids upwards of 500 ppm and because the small size and specific gravity of these plant structures make them difficult to filter and difficult to concentrate, by any automatic filter mechanism.

Dry extraction methods have been used to remove and isolate specific plant parts, such as small structure like trichomes and lupulins, from plant material. However, these extraction methods have drawbacks. For example, dry extraction methods using dry ice, tumbling and sieves can damage trichomes and their chemical products. Further, these methods also recover only a fraction of the available trichomes; they may recover only 20% to 30% of the trichomes.

Figure 26:
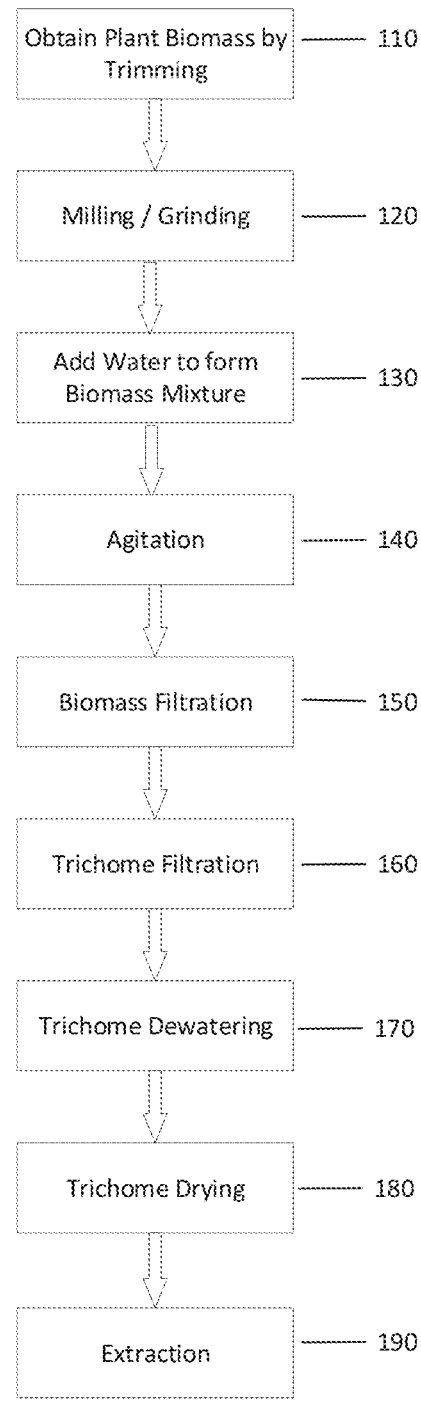
FIG. 26 illustrates an embodiment of a processes for removing and isolating small structures like trichomes from plant material.

The wet extraction methods as described herein have been found to produce higher yields of plant parts such as trichomes, may be performed at consistent process temperatures and are less likely to damage the plant parts, such as through heat or abrasion. In some embodiments a wet extraction process is carried out to purify and concentrate desired plant parts, such as trichomes as illustrated in FIG. 26.

Plant biomass may be prepared by trimming plants 110 to obtain plant material comprising the structures of interest, such as trichomes. In some embodiments cannabis plants are trimmed to obtain biomass comprising trichomes. The plant biomass may optionally be milled or ground 110. For example, cannabis plant biomass may be milled or ground to produce smaller pieces. The plant material is combined with liquid to form a liquid plant biomass mixture 130. In some embodiments the liquid is water. The water may comprise one or more additives. For example, the water may comprise one or more additives that aid in the release of the desired plant parts. Thus, in some embodiments cannabis plant biomass is combined with water to form a liquid plant biomass mixture. In some situations the use of chilled water may be advantageous. For example, chilled water may advantageously make trichomes brittle and more easily removed from the surface of the plant. Thus, in some embodiments cannabis plant biomass is combined with chilled water to form a liquid plant biomass mixture. In some embodiments the water is cooled to below room temperature prior to mixing with the plant biomass. In some embodiments the water is ice water. In some embodiments the water is less than 25° C., less than 20° C., less than 15° C., less than 10° C. or less than 5° C. and at least above 0° C. In some embodiments the plant biomass mixture is cooled to below room temperature. In some embodiments the plant biomass mixture is maintained at a temperature below room temperature during processing.

In some embodiments a ratio of water (or other liquid) to plant material is about one pound of plant material to 1 gallon of water, but other ratios may also be used, for example a 2:1, 3:1, 4:1, 5:1 or greater, or 1:2, 1:3, 1:4, 1:5 or greater ratio of pounds of plant material to gallons of water.

In some embodiments the liquid plant biomass mixture is agitated 140. For example, a plant biomass mixture prepared from cannabis may be agitated to release the trichomes (or other structures) from the plant material. In some embodiments the mixture may be placed in a container and agitated by mixing. In some embodiments the mixture may be agitated by passing it through a pump or other high shear device, for example a nozzle, screen or centrifuge.

In some embodiments the mixture is filtered to remove undesirable biomass 150 prior to filtering to collect the desired plant part. In some embodiments a biomass mixture prepared from cannabis plants is filtered to remove undesirable biomass. For example, the plant mixture may be passed through one or more filters sized to remove undesirable plant parts while allowing the plant part of interest to pass through. In some embodiments filtration through a relatively large filter may be carried out. In some embodiments filtration through a series of filters may be carried out. In some embodiments the filtration may be through a series of smaller and smaller filters. In some embodiments the filtration may be a manual process. In some embodiments the filtration process comprises passing the plant biomass mixture through one or more filtration screens comprising pores of greater than 25 microns, greater than 50 microns, greater than 100 microns, greater than 150 microns or greater than 200 microns. In some embodiments the filtration is performed using woven mesh filter bags. For example, a 220 micron filter bag may be used to remove much of the undesired plant material, such as non-trichome plant material. Other filter bags, for example a 160 micron bag, may also be used to remove plant material, for example subsequent to the 220 micron filter bag. Subsequent filtration may be carried out using a 45 micron bag and/or a 25 micron bag. These filter bags may be used alone or in combination to remove plant material and isolate the desired plant part, such as trichomes or lupulins.

Following removal of undesirable plant material, embodiments of the filter apparatus described herein are used to separate, concentrate and/or collect the desired plant parts, such as trichomes or lupulins 160. In some embodiments the biomass mixture prepared from cannabis plants is provided to a filter apparatus as described herein to collect the trichomes. In some embodiments the plant biomass mixture that is processed in the apparatus comprises greater than 100 ppm solids, greater than 200 ppm solids, greater than 300 ppm solids, greater than 500 ppm solids, greater than 600 ppm solids, greater than 700 ppm solids, greater than 800 ppm solids, greater than 900 ppm solids or greater than 1000 ppm solids. In some embodiments the plant biomass mixture may comprise from about 100 to 10000 ppm solids. In some embodiments the biomass mixture comprises a concentration of trichomes or lupulins of 500 ppm to 10000 ppm, or from 1000 ppm to 5000 ppm, but the concentration may be higher or lower. In some embodiments the plant biomass mixture comprises at least 500 ppm trichomes or lupulins. In some embodiments the plant biomass mixture comprises greater than 500 ppm trichomes or lupulins.

The plant biomass mixture is passed through a filtration device comprising a housing and a filter as described herein. In some embodiments the filter is an annular filter. In some embodiments the plant biomass mixture is passed continuously through the filtration device. In passing through the filtration device, the mixture is passed through a filter screen which allows for the isolation and collection of the desired components, such as trichomes or lupulins. In some embodiments other plant material is not collected.

In some embodiments the filter material is a wire screen. In some embodiments the filter material is a wedgewire filter screen. In some embodiments the filter material has a nominal gap width of 15 microns, but in some embodiments other filter screens and other gap widths may also be used, as discussed above. In some embodiments a filter material has a gap width of about 10 to 50 microns, about 10-25 microns or about 15 microns. The particular screen size can be selected based on the plant parts that are to be filtered from the plant biomass mixture and collected. In some embodiments the filter material forms a hollow filter as described above.

In some embodiments the plant biomass mixture is provided to the filter through a vertical distributor located within a hollow annular filter as described above. In some embodiments the distributor rotates. In some embodiments the biomass mixture is provided to the filter continuously during the filtration of the desired plant parts.

In some embodiments a rotating cleaning assembly as described herein is used to continuously wipe the surface of the filter material while the plant biomass mixture is provided. The rotating cleaning assembly cleans the filter screen and allows fluid to continuously pass through the filter screen.

Plant parts, such as trichomes or lupulins, are removed from the plant biomass mixture and are collected at one end of the housing. In some embodiments, a purge valve may be opened intermittently to allow collection of the desired plant parts, though other operational modes may also work. For example, a purge opening may remain open to allow the desired plant parts to continuously pass out of the housing and be collected. As plant parts collect at the bottom of the housing this may produce increased torque on the motor and thus increased current draw by the motor. This increased current draw may be monitored to actuate the opening of a purge valve. The purge valve may also be opened on a timed basis to remove collected plant parts at desired intervals.

In some embodiments, more than 50%, 60%, 70%, 80%, 90%, 95% or even 99% of the desired plant parts are removed from a mixture comprising the desired plant parts and other plant material (the plant biomass mixture). In some embodiments undesired plant parts, such as immature, underdeveloped trichomes are not collected. In some embodiments trichomes are processed from cannabis biomass and greater than 90%, 95% or 99% of the desired plant parts are collected from the starting plant biomass.

In some embodiments the collected material comprises more than 50%, 60%, 70%, 80%, 90%, 95% or even 99% of the desired plant part. For example, in some embodiments more than 50%, 60%, 70%, 80%, 90%, 95% or even 99% of the collected material comprises trichomes or lupulins by weight.

In some embodiments, the collected plant parts are processed further to obtain desired components. For example, in some embodiments collected plant parts such as trichomes or lupulins are dewatered 170. In some embodiments they are dewatered using a filter bag, dewatering sack, belt filter press or other device. The collected plant parts may also be dried. In some embodiments the filtration and dewatering step may produce a sludge having a concentration of 10% to 50% solids. This sludge may then be dried 180 using any number of techniques, for example dewatering bags, freeze drying, air drying, spray drying or other techniques known to someone skilled in the art. In some embodiments trichomes collected from the cannabis biomass are dewatered 170 and dried 180.

In some embodiments after collection, and after dewatering and drying, if it is carried out, the plant parts are subsequently processed to extract desired components 190. For example, dried plant parts may be further processed using any number of extraction techniques, some of which are mentioned above. For example desired components may be extracted in some embodiments by using an extraction technique such as supercritical $CO_2$ extraction, ethanol extraction or butane extraction. In some embodiments trichomes obtained by filtration of the cannabis biomass may be processed 190 to extract one or more terpenes and/or cannabinoids, such as CBD. In some embodiments purified lupulins may be processed to extract lupulin or lupinol.

EXAMPLE

Figure 27:
FIG. 27 is a photograph of a trichome sludge resulting from the filtration process.
Figure 28:
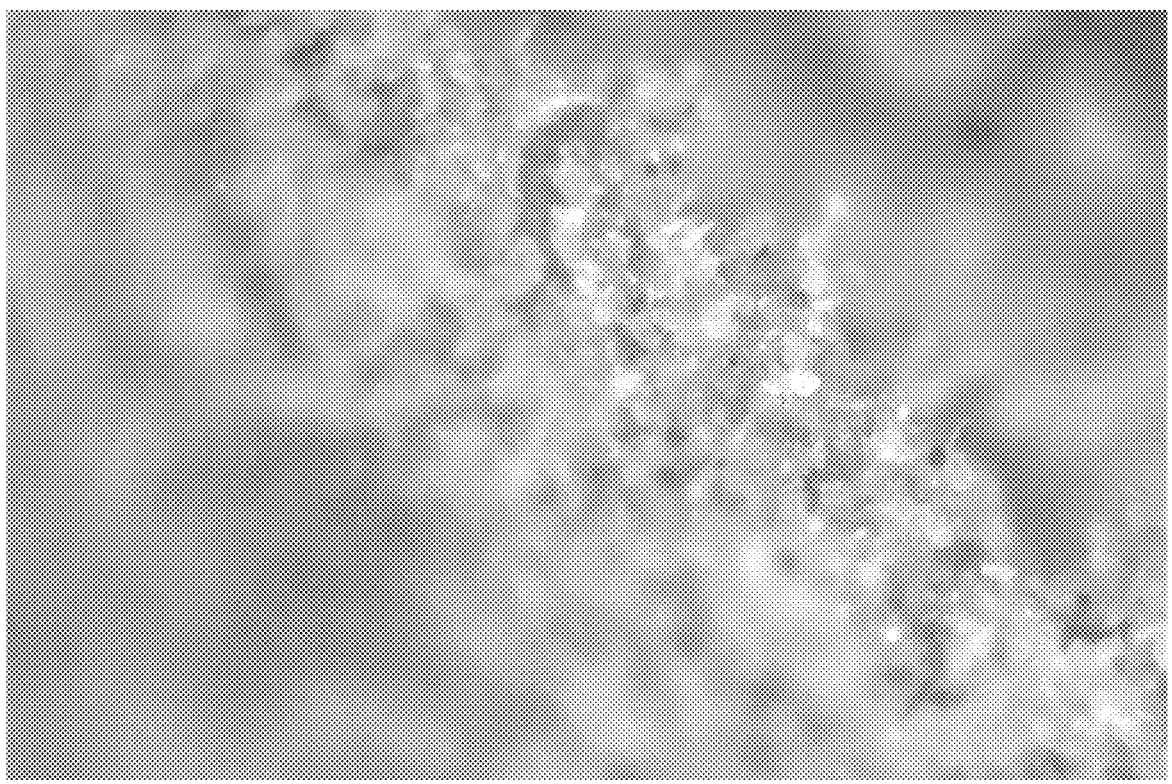
FIG. 28 illustrates mature trichomes that are isolated from a water mixture by the methods and apparatus described herein.
Figure 29:
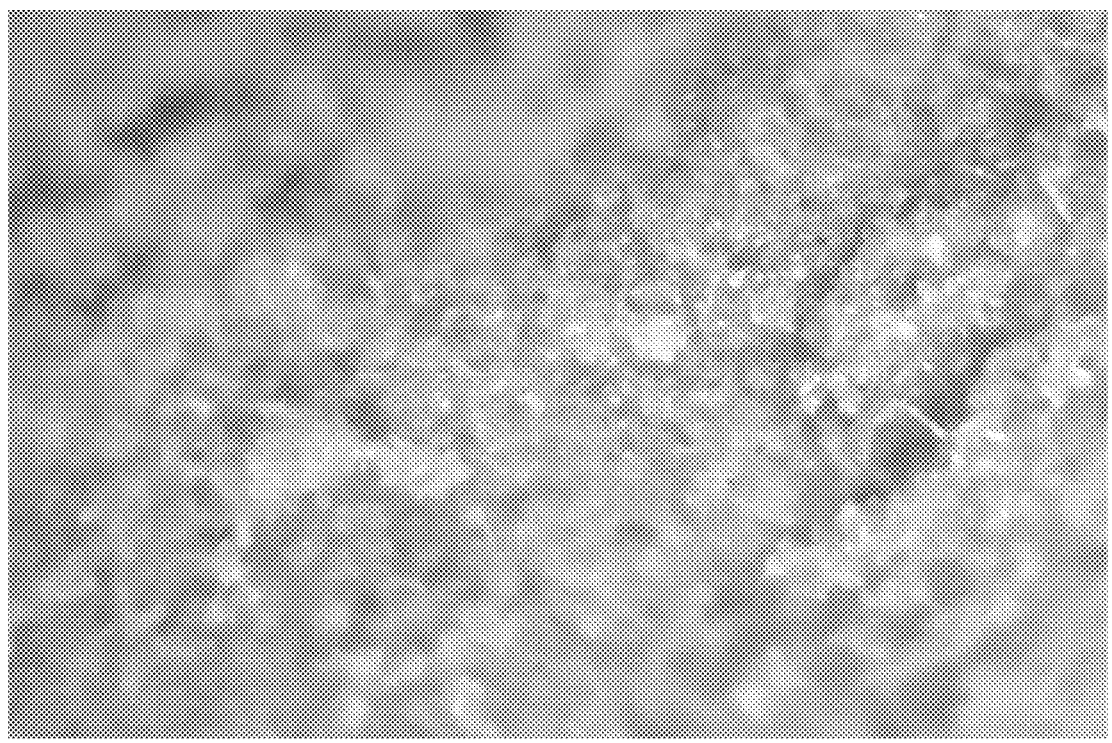
FIG. 29 illustrates immature, undeveloped trichomes that pass through the filter and are not collected by the methods and apparatus described herein.

Cannabis plants were trimmed and the biomass collected. After milling and grinding the biomass was combined with ice water and agitated. The mixture was passed through a filtration device comprising a wedgewire filter screen having a nominal gap width of 15 microns to isolate the trichomes. The filtration device comprised a rotating cleaning assembly, which efficiently cleaned the filter screen and allowed fluid to continuously pass through the filter screen. Trichomes were collected and concentrated at one end of the housing. A purge valve was opened intermittently to allow a trichome sludge, shown in FIG. 27, to pass out of the housing. Greater than 99% of the mature trichomes (FIG. 28) was removed from the water mixture comprising trichomes and other plant material. Immature, underdeveloped trichomes were excluded (FIG. 29) and were not collected with the mature trichomes. These immature trichomes are less desirable than the larger developed trichomes.

The concentrated trichome sludge may be further dewatered, for example using a traditional filter bag, dewatering sack, belt filter press or other device. The trichomes can be dried using one of many available drying processes, for example air drying or freeze drying. The dried trichomes may then be processed to extract the desired components, such as terpenes or cannabinoids, for example by using an extraction technique such as supercritical $CO_2$ extraction, ethanol extraction or butane extraction. In some embodiments THC and/or CBD is extracted from the purified trichomes.

What is claimed is:

1. A method of collecting trichomes from plant biomass comprising:
   providing a plant biomass mixture comprising greater than 500 ppm trichomes and water;
   providing a filtration device comprising:
      a housing having an unfiltered inlet and a filtered outlet;
      an annular filter located within the housing comprising a filter material having a gap width of about 10 to 25 microns; and
      a rotating cleaning assembly located inside the annular filter and comprising a distributor;
   filtering trichomes from the plant biomass by directing the mixture through the distributor to an inside surface of the filter;
   passing the plant biomass mixture through the filter;
   rotating the cleaning assembly inside the filter such that the inside surface of the filter is cleaned;
   and collecting filtered material comprising trichomes at the filtered outlet,
   wherein greater than 90% of the trichomes are removed from the liquid plant biomass mixture and collected in the filtered material.

2. The method of claim 1, wherein the plant biomass mixture is continuously fed through the distributor to the inside surface of the filter during filtering.

3. The method of claim 1, wherein the filtered material is continuously collected at the filtered outlet during filtering.

4. The method of claim 1, wherein the cleaning assembly is continuously rotated during filtering.

5. The method of claim 1, wherein more than 50% of the collected filtered material is trichomes by weight.

6. The method of claim 1, additionally comprising preparing the liquid plant biomass mixture by harvesting plant biomass from one or more cannabis plants and mixing the plant biomass with water at a temperature below 20° C.

7. The method of claim 1, additionally comprising filtering the plant biomass mixture through one or more filters each comprising pores of at least 100 microns prior to filtering.

8. The method of claim 1, additionally comprising agitating the plant biomass mixture prior to filtering.

9. The method of claim 1, additionally comprising dewatering the filtered material.

10. The method of claim 1, additionally comprising drying the filtered material.

11. The method of claim 10, additionally comprising extracting one or more terpenes and/or cannabinoids from the dried material.

12. The method of claim 11, wherein CBD and/or THC is extracted from the dried material.

13. The method of claim 11, wherein the one or more terpenes or cannabinoids are extracted by supercritical $CO_2$ extraction, ethanol extraction or butane extraction.

14. The method of claim 1, wherein the cleaning assembly comprises a wiper located within the filter.

15. The method of claim 14, wherein the wiper is spiral.

16. The method of claim 14, wherein the wiper comprises a brush.

17. The method of claim 1, wherein the filter material comprises an electroformed screen.

18. A method of purifying one or more plant parts from plant biomass comprising:
   providing plant biomass comprising the one or more plant parts;
   mixing the plant biomass with water to form a plant biomass mixture;
   providing a filtration device comprising:
      a housing comprising a filter having a gap width of about 10 to 25 microns; and
      a cleaning assembly;
   filtering the plant parts from the plant biomass mixture by continuously feeding the plant biomass mixture through the filter;
   continuously cleaning the filter while filtering using the cleaning assembly;
   and collecting the one or more plant parts,
   wherein greater than 90% of the plant parts in the plant biomass are collected.

19. The method of claim 18, wherein the filter is annular and the cleaning assembly is rotated within the annular filter.

20. The method of claim 19, wherein the one or more plant parts are trichomes or lupulins.

* * * * *